(12) United States Patent
Nakanishi

(10) Patent No.: US 6,790,451 B2
(45) Date of Patent: Sep. 14, 2004

(54) COSMETIC MATERIAL

(75) Inventor: Tetsuo Nakanishi, Gunma-ken (JP)

(73) Assignee: Shin-Etsu Chemical Co., Ltd., Tokyo (JP)

(*) Notice: Subject to any disclaimer, the term of this patent is extended or adjusted under 35 U.S.C. 154(b) by 98 days.

(21) Appl. No.: 10/011,320

(22) Filed: Dec. 11, 2001

(65) Prior Publication Data
US 2002/0114771 A1 Aug. 22, 2002

(30) Foreign Application Priority Data
Dec. 11, 2000 (JP) .................................. 2000-375585

(51) Int. Cl.$^7$ .......................... A61K 6/00; A61K 7/00; C07F 7/04; C07F 7/08; C07F 7/21
(52) U.S. Cl. .................. 424/401; 556/450; 556/451; 556/465; 556/443; 556/434
(58) Field of Search ................. 424/401; 556/450, 556/451, 465, 443, 434

(56) References Cited

U.S. PATENT DOCUMENTS 5,412,004 A * 5/1995 Tachibana et al. ............. 524/27
5,557,000 A * 9/1996 Minemura ................... 556/434

FOREIGN PATENT DOCUMENTS

EP 0545002 A1 6/1993
EP 1062944 A1 12/2000

* cited by examiner

*Primary Examiner*—Russell Travers
(74) *Attorney, Agent, or Firm*—Millen, White, Zelano, Branigan, P.C.

(57) ABSTRACT

A cosmetic material comprising as essential cosmetic constituents (A) a silicone-branched silicone compound and (B) a silicone-branched polyether-modified silicone compound.

35 Claims, No Drawings

COSMETIC MATERIAL

FIELD OF THE INVENTION

The present invention relates to a cosmetic material containing a specific silicone compound, and more particularly to a cosmetic material which can ensure a feeling of refreshment for users thereof, and besides, which can have high stability in an emulsified state and high transparency.

BACKGROUND OF THE INVENTION

Makeup is generally smeared with secretion from humans, such as sweat, tear or sebum. In particular, the leading cause of makeup spoilage consists in that powders in a cosmetic material are wetted excessively by sebum secreted from the skin in addition to unctuous agents compounded in the cosmetic material. Therefore, with the intention of reducing the unctuous agents remaining on the skin after makeup is done, it has been attempted to use volatile oils, such as octamethylcyclotetrasiloxane and decamethylcyclopentasiloxane, as a part of the unctuous agents compounded in a cosmetic material.

Further, the rub and the water given to the makeup constitute external factors inhibiting the makeup effect from lasting long. For the purpose of preventing the makeup from coming off by contact with aqueous substances, such as sweat and tears, or maintaining the skin protecting effect by preventing a loss of water-soluble components and sebum in the skin, it has been carried out to heighten the water repellency by mixing a silicone oil in the cosmetic material. In recent years, silicone oils have been used as unctuous agents in compositions of water-in-oil emulsion type for the purpose of imparting a refreshing and less tacky feel and excellent water repellency to the compositions. In the silicon oil-containing water-in-oil type emulsions, however, it has hitherto been difficult to ensure good stability by the use of traditional polyoxyalkylene fatty acid ester-type emulsifiers.

Therefore, methods of using, as surfactants for the emulsions of silicone oil-containing water-in-oil type, polyoxyalkylene-modified organopolysiloxanes (or polyether-modified silicones) having good compatibility with silicone oils are proposed, e.g., in Tokkai Sho 61-293903, Tokkai Sho 61-293904, Tokkai Sho 62-187406, Tokkai Sho 62-215510 and Tokkai Sho 62-216635 (wherein the term "Tokkai" means an "unexamined published Japanese patent application").

When emulsions are prepared with the intention of using them as cosmetics, it is frequent that ester oils and hydrocarbon oils are used as unctuous agents in addition to silicone oils. In these emulsions containing mixed oils, however, the foregoing polyether-modified silicones have inferior emulsifying capabilities, so they have a drawback of being insufficient to ensure satisfactory stability in such water-in-oil type emulsions.

As a solution to such a problem, the method of using as an emulsifier the organopolysiloxanes having both long-chain alkyl and polyoxyalkylene groups, which are represented by the following formula, is proposed in Tokkai Sho 61-90732:

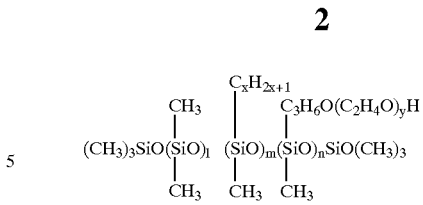

The foregoing organopolysiloxane compounds have excellent emulsifying capabilities in mixed oil systems rich in ester oils and hydrocarbon oils, but in silicone oil-rich mixed oil systems they often have great difficulties in stabilizing emulsions so as not to vary with a lapse of time. Under these circumstances, it has been desired to develop emulsifiers having suitability for cosmetics use and capabilities of sufficiently emulsifying any of unctuous agents mixed in general cosmetic materials, including silicone oils, ester oils and hydrocarbon oils, to ensure storage stability in the emulsions prepared.

SUMMARY OF THE INVENTION

As a result of our intensive studies of emulsifiers suitable for cosmetics use, it has been found that, when a silicone compound prepared by introducing both polyoxyalkylene and silicone compounds to organohydrogenpolysiloxane through the use of addition reaction is employed as an emulsifier, it can have a strong emulsifying capability because of its very high affinity for silicone oils and ensure high stability in the resultant emulsions. In addition, it has also been found that a silicone compound prepared by further introducing organic groups having long-chain alkyl moieties to the foregoing polyoxyalkylene- and silicone compounds-introduced organohydrogenpolysiloxane through the use of addition reaction can show excellent capability as an emulsifier for any of unctuous agents generally used in cosmetic materials, including silicone oils, ester oils and hydrocarbon oils, because of its high affinities for all of these oils, and so can function as an excellent emulsifier to ensure satisfactory storage stability in the resultant emulsions and be highly effective for cosmetics use. Moreover, it has been found that when the branched polyether-modified silicone compound is used as an activator and a branched silicone compound is used as an oil component the resultant emulsion can have further enhanced stability.

With respect to such a branched silicone compound, although JP-A-7-197055 describes that a silicone oil prepared by addition reaction between an organohydrogenpolysiloxane and a silicone compound functions as an oil for mechanical use and has good low temperature characteristics, we have found that the branched silicone compound as such a silicone oil can be used effectively for cosmetic materials. Further, we have found that, when the foregoing silicone compound has its molecular weight in a low molecular weight region, it can produce excellent effect in cleansing sebum stains and makeup stains from cosmetics of the type which are hard to come off, and can be instrumental in preparing a skin-cleansing composition having a very good touch during and after cleansing treatment.

Therefore, an object of the invention is to provide a cosmetic material highly stable and transparent in an emulsified state and capable of giving a refreshing feel to users thereof.

The object described above is attained with a cosmetic material comprising as essential cosmetic components (A) a silicone-branched silicone compound and (B) a silicone-branched polyether-modified silicone.

DETAILED DESCRIPTION OF THE INVENTION

Embodiments of the invention are described below in detail.

(I) Branched Silicon Compound

A branched silicone compound represented by the following formula (1) is usable as the present silicone-branched silicone compound (A):

$$R^1_a R^2_b SiO_{(4-a-b)/2} \quad (1)$$

Each $R^1$ in the above formula is independently a hydrogen atom, an alkyl group containing 1 to 30 carbon atoms (e.g., methyl, ethyl, propyl, butyl, pentyl, hexyl, heptyl, octyl, nonyl or decyl), a cycloalkyl group (e.g., cyclopentyl or cyclohexyl), an aryl group (e.g., phenyl or tolyl), an aralkyl group (e.g., benzyl or phenetyl), a fluorinated alkyl group (e.g., trifluoropropyl or heptadecafluorodecyl), an amino-substituted alkyl group (e.g., 3-aminopropyl or 3-[(2-aminoethyl)amino]propyl), or a carboxyl-substituted alkyl group (e.g., 3-carboxypropyl).

Further, a part of $R^1$ groups may be organic groups represented by formula $-C_cH_{2c}-O-(C_2H_4O)_d(C_3H_6O)_e R^3$, which is referred to as formula (2) hereinafter. In formula (2), $R^3$ is a monovalent hydrocarbon group containing 10 to 30 carbon atoms or an organic group represented by $R^4-(CO)-$, $R^4$ is a monovalent hydrocarbon group containing 9 to 30 carbon atoms, and c, d and e are each an integer and fall within the following ranges: $0 \leq c \leq 15$, $0 \leq d \leq 50$, $0 \leq e \leq 50$. Specifically, these organic groups are, e.g., alcohol residues or alkenyl ether adduct residues. Examples of these residues are described below.

When c is 0, the formula (2) is $-O-(C_2H_4O)_d(C_3H_6O)_e R^3$. Further, it becomes $-O-R^3$ in the case of e=0 and d=0, and represents a residue of higher alcohol such as cetyl alcohol, oleyl alcohol or stearyl alcohol, or a residue of higher fatty acid.

In a case of d, $e \geq 1$, on the other hand, the formula (2) represents an alcohol residue of higher alcohol/alkylene oxide adduct (having OH at the end).

When c is 1 or 2 the formula (2) is $-C_cH_{2c}-O-(C_2H_4O)_d(C_3H_6O)_e R^3$, and this group can be introduced by dehydrohalogenation reaction between Si—OH group and $X(CH_2)_n-O-(C_2H_4O)_d(C_3H_6O)_e R^3$ (wherein X is halogen) to provide a silicone-branched silicone compound (A).

In the case of $c \geq 3$, the $-C_cH_{2c}-O-(C_2H_4O)_d(C_3H_6O)_e R^3$ group is a higher alcohol or higher fatty acid-alkenyl ether or alkenyl ester addition reaction residue, or a polyalkylene oxide adduct thereof.

Each $R^2$ is independently a silicone compound residue represented by the following formula (3):

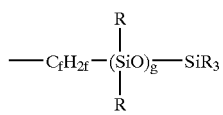

(3)

wherein each R is independently an alkyl group containing 1 to 30 carbon atoms, an aryl group, an aralkyl group or a fluorinated alkyl group, f is an integer of from 1 to 5, and g is an integer of from 0 to 500, preferably from 3 to 100. For instance, f has a value of 2 when the synthesis is performed by reaction between vinyl and SiH groups. When g is an integer greater than 500, such a silicone compound is liable to have inferior reactivity with a compound constituting the main chain.

In formula (1), a is a number of from 1.0 to 2.5, preferably from 1.2 to 2.3, and b is a number of from 0.001 to 1.5, preferably from 0.05 to 1.0.

In the invention, the suitable weight average molecular weight for a silicone compound represented by formula (1), though it has no particular limits, is from 500 to 200,000, preferably from 1,000 to 100,000.

The present silicone compound represented by formula (1) can be synthesized with ease by addition reaction between organohydrogenpolysiloxane and a silicone compound represented by the following formula (i) and, if desired, an olefin compound as well in the presence of a platinum or rhodium catalyst, or by reaction between a silicone compound represented by formula (ii) and organovinylsiloxane:

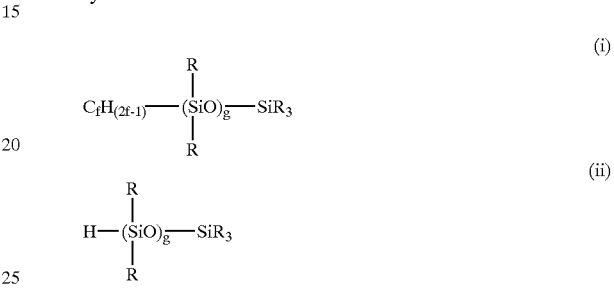

wherein R, f and g have the same meanings as in formula (3) respectively.

The organopolysiloxane to constitute the main chain of the present silicone compound may have a straight-chain structure or a cyclic structure. The suitable mixing ratio between a main-chain polysiloxane and a silicone compound represented by formula (i) or (ii) is from 0.5 to 2.0, preferably from 0.8 to 1.2, expressed in terms of the quantity by mole of the terminal unsaturated group per mole of SiH groups. The addition reaction is carried out effectively in the presence of a platinum catalyst or a rhodium catalyst. Suitable examples of such a catalyst include chloroplatinic acid, alcohol-modified chloroplatinic acid and chloroplatinic acid-vinylsiloxane complex. Additionally, the amount of catalyst used, though it may be a conventional catalytic amount, is desirably at most 50 ppm, particularly desirably at most 20 ppm, based on the platinum or the rhodium.

The addition reaction may be carried out in an organic solvent, if needed, but it is advantageous for the reaction to be performed under a solvent-free condition. Examples of an organic solvent usable therein include aliphatic alcohol compounds, such as methanol, ethanol, 2-propanol and butanol; aromatic hydrocarbons, such as toluene and xylene; aliphatic or alicyclic hydrocarbons, such as n-pentane, n-hexane and cyclohexane; and halogenated hydrocarbons, such as dichloromethane, chloroform and carbon tetrachloride. The addition reaction has no particular restriction as to its reaction conditions. However, it is desirable that the addition reaction be performed for 1 to 10 hours under reflux.

Other branched silicone compounds usable as the present silicone-branched silicone compound (A) can be synthesized using specified siloxane compounds as starting materials in accordance with any of the following three methods.

Specifically, a first synthesis method comprises using as one of starting materials a branched silicone (4) containing $[R^5_3SiO_{1/2}]_h$ units (M units) and $[R^5SiO_{3/2}]_i$ units (T units) in proportions that the i/h ratio falls within the range of 0.3 to 1.5. (The branched silicone (4) is referred to as "MT polymer" hereinafter.)

Each $R^5$ in those units is independently a hydrogen atom or an organic group selected from 1–30C alkyl groups, aryl groups, aralkyl groups, fluorinated alkyl groups, amino-substituted alkyl groups, carboxyl-substituted alkyl groups or 1–6C alkoxy groups. Examples of such an organic group include alkyl groups, such as a methyl group, an ethyl group, a propyl group, a butyl group, a pentyl group, a hexyl group, a heptyl group, an octyl group, a nonyl group and an decyl group; cycloalkyl groups, such as a cyclopentyl group and a cyclohexyl group; aryl groups, such as a phenyl group and a tolyl group; aralkyl groups, such as a benzyl group and a phenetyl group; fluorinated alkyl groups, such as a trifluoropropyl group and a heptadecafluorodecyl group; aminoalkyl groups, such as a 3-aminopropyl group and a 3-[(2-aminoethyl)amino]propyl group; carboxyalkyl groups, such as a 3-carboxypropyl group; and alcohol residues, such as a methoxy group, an ethoxy group and an allyloxy group. In particular, it is preferable that at least 50% of $R^5$ groups in the branched silicone (4) be methyl or phenyl groups.

The i/h ratio is required to fall within the range of 0.3 to 1.5. Preferably, the i/h ratio is from 0.6 to 1.2. When the i/h ratio is smaller than 0.3 or greater than 1.5, a large quantity of remaining alkoxy or hydroxyl groups are present in a branched silicone; as a result, production of the intended silicone-branched silicone compound by equilibration reaction using such a branched silicone cannot be performed consistently. In the invention, it is most desirable that the i/h ratio be 1. This is because, when the i/h ratio is 1, a polysiloxane compound having the intended molecular weight can be synthesized by polymerization under a general condition for acid or alkali equilibration reaction without consideration of M-unit source for branched polysiloxane.

An MT polymer can be prepared by dissolving an organosilane or siloxane to constitute the M unit, e.g., $(CH_3)_3SiCl$, $(CH_3)_3SiOSi(CH_3)_3$ or $(CH_3)_3SiOH$, and an organosilane to constitute the T unit, e.g., trichloromethylsilane or trialkoxymethylsilane, in alcohol or a hydrocarbon solvent, such as hexane, toluene or xylene, and adding water or an acid thereto to cause hydrolysis therein. Examples of an acid used for hydrolysis include sulfuric acid, sulfurous acid, fuming sulfuric acid, p-toluenesulfonic acid, methanesulfonic acid, trifluoromethanesulfonic acid, hydrochloric acid, and phosphoric acid. The acid as a catalyst may be added in a small amount. Preferably, it is added in a proportion of 0.001 to 10 weight %.

The removal of the acid after hydrolysis is generally effected by neutralization with carbonate, hydrogen carbonate or hydroxide of ammonium, alkali metal or alkaline-earth metal, or by washing. When the reaction solution comes to have too high alkalinity, however, silanol groups remaining unreacted adsorb alkali metals. As a result, it sometimes occurs that the reaction system does not become neutral even by neutralization with hydrochloric acid or citric acid. Therefore, it is appropriate that the neutralization of MT polymer be carried out as follows: An aqueous alkali solution is added in advance in an insufficient amount (85 to 95% of the required amount for neutralization of the acid catalyst) to perform partial neutralization, and then a solid salt, such as an alkali metal carbonate, is added in an amount more than equivalent weight to complete the neutralization.

When the neutralization is carried out using an aqueous alkali solution in an amount more than equivalent weight, it is advantageous to adopt the following process. Specifically, it is checked to be sure that the reaction solution is alkaline, and then the reaction solution is rendered weakly acidic by the use of a weak acid, such as citric acid, followed by neutralization with a weak base, such as a carbonate of alkali or alkaline-earth metal or a ammonium salt, to make the pH of the reaction solution neutral. After neutralizing the acid, the alcohol compounds produced and excessive water are removed by heating under atmospheric pressure or reduced pressure. Thus, the intended MT polymer is obtained.

When an MT polymer is produced using starting materials in proportions of 1:1 (i/h=1/1) and according to the aforementioned method, the T/M ratio of the polymer produced becomes approximate to 1/1 and the silanol content can be controlled to 20 mole % or below.

Equilibration reaction between the foregoing MT polymer and a silicone compound represented by the following formula (5) or (6) is carried out using them in proportions determined depending on the molecular weight and viscosity desired for a compound to be synthesized:

(5)

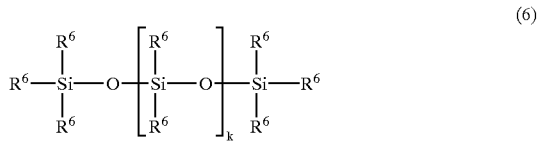

(6)

In the above formulae, each $R^6$ is independently a hydrogen atom or an organic group selected from 1–30C alkyl groups, aryl groups, aralkyl groups, fluorinated alkyl groups, amino-substituted alkyl groups or carboxyl-substituted alkyl groups. Examples of such an organic group include alkyl groups, such as a methyl group, an ethyl group, a propyl group, a butyl group, a pentyl group, a hexyl group, a heptyl group, an octyl group, a nonyl group and an decyl group; cycloalkyl groups, such as a cyclopentyl group and a cyclohexyl group; aryl groups, such as a phenyl group and a tolyl group; aralkyl groups, such as a benzyl group and a phenetyl group; fluorinated alkyl groups, such as a trifluoropropyl group and a heptadecafluorodecyl group; amino-substituted alkyl groups, such as a 3-aminopropyl group and a 3-[(2-aminoethyl)amino]propyl group; and carboxyl-substituted alkyl groups, such as a 3-carboxypropyl group. Especially preferred substituents as $R^6$ groups are methyl groups and phenyl groups.

The cyclic silicone compound of formula (5) is a cyclic polysiloxane compound whose m value as polymerization degree is in the range of 3 to 10. In the invention, hexamethylcyclotrisiloxane, octamethylcyclotetrasiloxane and decamethylcyclopentasiloxane are preferred in particular as the compound of formula (5).

The silicone compound of formula (6) is a straight-chain organosiloxane whose p value as polymerization degrees is in the range of 0 to 100. In the invention, hexamethyldisiloxane is preferred in particular as the compound of formula (6).

Examples of a catalyst usable in the equilibration reaction include acid catalysts, such as sulfuric acid, sulfurous acid, fuming sulfuric acid, p-toluenesulfonic acid, methanesulfonic acid, trifluoromethanesulfonic acid, hydrochloric acid and phosphoric acid; and alkaline catalysts, such as hydroxides of alkali metals (e.g., NaOH and KOH) and reaction products of dimethylpolysiloxane with alkali metals. The proportion of a catalyst used to polysiloxanes as the reactants is from about 100 ppm to about 10,000 ppm. Although the reaction condition depends on the catalyst used, the reaction temperature is generally chosen from the range of 0° C. to 100° C. in the case of using an acid catalyst, while in the case of using an alkaline catalysst it is generally chosen from the range of 100° C. to 180° C. Additionally, when the reactants are silicone compounds having hydrosilyl groups as their functional groups, acid catalysts are used, but alkaline catalysts are not used.

A second synthesis method is a method of using a silicone compound represented by the following formula (7) as a branch source:

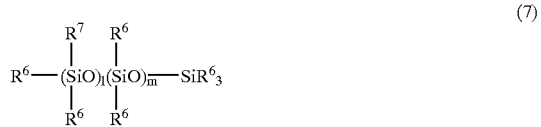

(7)

In the above formula, $R^6$ has the same meaning as in formulae (5) and (6), and each $R^7$ is independently a hydrolyzable group selected from a hydroxyl group or 1–6C alkoxy groups. Specifically, $R^7$ is a hydroxyl group, a methoxy group, an ethoxy group, a propoxy group, an isopropoxy group or a butoxy group.

And l is an integer of from 1 to 100, while m is an integer of from 0 to 1,000. Of these polysiloxane compounds, 1,1,1,3,5,7,7,7-octamethyl-3,5-dihydroxytetrasiloxane is preferred over the others. By using this polysiloxane compound in an amount of 1 mole, it becomes possible to introduce 2 moles of MT source. This polysiloxane compound can be easily produced according to a known method of, e.g., causing dehydrogenation reaction between the corresponding methylhydrogenorganopolysiloxane and water in the presence of a palladium-carbon catalyst.

Polymerization reaction between a silicone compound represented by formula (7) and a silicone compound represented by formula (5) or/and a silicone compound represented by formula (6) can be performed in the same manner as the aforementioned polymerization reaction using a branched silicone compound (4).

A third synthesis method is a method of using as a branch source a polysiloxane compound represented by the following formula (8):

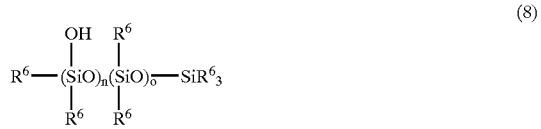

(8)

wherein $R^6$ has the same meaning as in formula (7), n is an integer of from 1 to 500, and o is an integer of from 0 to 500.

Specifically, the polysiloxane compound (8) is produced in advance by preparing methylhydrogenorganopolysiloxane having the desired polymerization degree and capable of providing the desired branch points, and then subjecting the organopolysiloxane prepared to dehydrogenation reaction with water in the presence of a palladium-carbon catalyst as in a known manner, and then subjected to ring-opening polymerization with hexamethylcyclotrisiloxane in accordance with a known method, thereby forming silicone branches. The ring-opening polymerization therein can be effected, e.g., by using a five-coordinate silicon complex catalyst or by living polymerization in the presence of an anionic polymerization catalyst.

(II) Polyether-modified Branched Silicone

A silicone compound represented by the following formula (9) is usable as the present silicone-branched polyether-modified silicone compound (B):

(9)

In the above formula, each $R^8$ is independently an organic group selected from 1–30C alkyl groups, aryl groups, aralkyl groups or fluorinated alkyl groups. Examples of these organic groups include alkyl groups, such as a methyl group, an ethyl group, a propyl group, a butyl group, a pentyl group, a hexyl group, a heptyl group, an octyl group, a nonyl group and a decyl group; cycloalkyl groups, such as a cyclopentyl group and a cyclohexyl group; aryl groups such as a phenyl group and a tolyl group; aralkyl groups such as a benzyl group and a phenetyl group; fluorinated alkyl groups such as a trifluoropropyl group and a heptadecafluorodecyl group; amino-substituted alkyl groups; and carboxy-substituted alkyl groups.

Further, $R^8$ may be an alkoxy group, an ester group, an alkenyl ether residue or an alkenyl ester residue represented by the following formula (10):

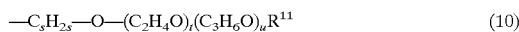

(10)

wherein $R^{11}$ is a 10–30C monovalent hydrocarbon group or an organic group represented by $R^{14}$—(CO)—; $R^{14}$ is a 9–30C monovalent hydrocarbon group; and t, u and s are each an integer and fall within the following ranges: $0 \leq s \leq 15$, $0 \leq t \leq 50$, $0 \leq u \leq 50$.

More specifically, in the case of s=0, t=0 and u=0, $R^8$ is a higher alkoxy group containing 10 to 30 carbon atoms, such as an oleyloxy group and a stearoxy group, or an ester group, such as an oleic acid ester group, a stearic acid ester group or a behenic acid ester group.

In the cases of $s \geq 1$, t=0 and u=0, it is preferable that s is 3, 5 or 11. In these preferable cases, $R^8$ is a residue of allyl ether, pentenyl ether or undecenyl ether. To be more concrete, such a residue becomes, e.g., an allyl stearyl ether residue, a pentenyl behenyl ether residue or an undecenyl oleyl ether residue depending on $R^{11}$. In the cases where t or u is not zero, an alkoxy group or an ester group is present via a polyoxyalkylene linkage in the group of formula (10).

When s is 0, the organic group of formula (10), irrespective of t and u, tends to have inferior hydrolysis resistance; while, when s is not smaller than 15, it becomes a cause of a strong smell of oil. Therefore, s is preferably within the range of 3 to 11.

In the invention, it is appropriate in particular that 50% or more, preferably at least 70%, of total $R^8$ groups be methyl groups. Additionally, all the $R^8$ groups may be methyl groups, if desired.

Each $R^9$ is independently a polyoxyalkylene group represented by the following formula (11):

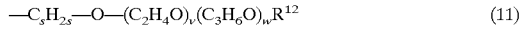

(11)

wherein s is an integer from 0 to 15, $R^{12}$ is a hydrogen atom, a 1–9C monovalent hydrocarbon group or an organic group represented by $R^{15}$—(CO)—, and $R^{15}$ is a 1–8C monovalent hydrocarbon group.

In formula (11), v is an integer of from 2 to 200, preferably from 5 to 100, and w is an integer of from 0 to 200, preferably from 0 to 100, provided that w+v is from 2 to 200, preferably from 5 to 100. In order that the polyether-modified silicone of formula (9) can have sufficient affinity for water in resultant water-in-oil emulsions, it is desirable that v and w satisfy a relation of $v/w \geq 1$.

Additionally, when the polyoxyalkylene moiety in formula (11) contains both ethylene oxide units and propylene oxide units, it may be a block or random copolymer of both of these units.

Each $R^{10}$ is independently an organosiloxane residue represented by the following formula:

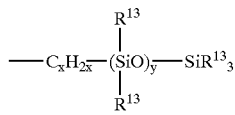  (12)

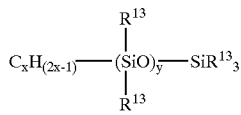  (15)

wherein each $R^{13}$ is independently an organic group selected from 1–30C alkyl groups, aryl groups, aralkyl groups or fluorinated alkyl groups. Examples of such an organic group include alkyl groups, such as a methyl group, an ethyl group, a propyl group, a butyl group, a pentyl group, a hexyl group, a heptyl group, an octyl group, a nonyl group and an decyl group; cycloalkyl groups, such as a cyclopentyl group and a cyclohexyl group; aryl groups, such as a phenyl group and a tolyl group; aralkyl groups, such as a benzyl group and a phenetyl group; and fluorinated alkyl groups, such as a trifluoropropyl group and a heptadecafluorodecyl group.

y is an integer of from 0 to 500, preferably from 3 to 100, and x is an integer of from 1 to 5. For instance, x is 2 when the $R^{10}$ group is a residue of the organosiloxane compound prepared by reaction of a vinyl group with a hydrogensiloxane compound. In the case where y is greater than 500, the organosiloxane compound tends to have a problem that its reactivity to organohydrogenpolysiloxane to constitute the main chain of the present silicone compound becomes low.

In formula (9), p is from 1.0 to 2.5, preferably from 1.2 to 2.3. When p is smaller than 1.0, the silicone compound is inferior in compatibility with unctuous agents, and so it fails to impart satisfactory stability to water-in-oil emulsions. When p is greater than 2.5, on the other hand, the silicone compound has poor affinity for water, so it also fails to ensure satisfactory stability in water-in-oil emulsions. q is from 0.001 to 1.5, preferably from 0.05 to 1.0. When q is smaller than 0.001, the silicone compound has poor affinity for water, and so it fails to ensure satisfactory stability in water-in-oil emulsions; while, when q is greater than 1.5, the silicone compound has too high affinity for water to impart satisfactory stability to water-in-oil emulsions. r is 0.001 to 1.5, preferably from 0.05 to 1.0. When r is smaller than 0.001, the silicone compound is inferior in compatibility with silicone oils, and so it fails to ensure satisfactory stability in water-in-oil emulsions. When r is greater than 1.5, on the other hand, the silicone compound has poor affinity for water, so it also fails to ensure satisfactory stability in water-in-oil emulsions.

When the present silicone compound of formula (9) is employed as an emulsifier, it has no particular restriction as to weight average molecular weight, but its weight average molecular weight is preferably in the range of 500 to 200,000, particularly 1,000 to 100,000.

When the present silicone compound of formula (9) is mixed in skin cleansing compositions, on the other hand, its appropriate weight average molecular weight is at most 4,000, preferably at most 2,000, particularly preferably at most 1,500.

The present silicone compound represented by formula (9) can be easily synthesized by subjecting organohydrogenpolysiloxane to addition reaction with organic compounds represented by the following formulae (13) and (14), a silicone compound represented by the following formula (15) and further, if desired, an alkylene compound in the presence of a platinum or rhodium catalyst:

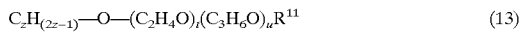  (13)

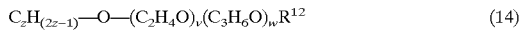  (14)

wherein $R^{11}$, $R^{12}$, $R^{13}$, t, u, v, w, x, and y have the same meanings as defined above respectively, and z is an integer of from 3 to 15.

The organohydrogenpolysiloxane used in the foregoing addition reaction may be either straight-chain or cyclic one. From the viewpoint of smooth progress of the addition reaction, straight-chain organohydrogenpolysiloxane is used to advantage.

In the addition reaction, it is appropriate that organohydrogenpolysiloxane be mixed with the foregoing organic compounds including the polyoxyalkylene compound of formula (14) and the silicone compound of formula (15), and further, if desired, an alkylene compound and/or the organic compound of formula (13) in proportions of from 1:2 to 2:1, preferably from 4:5 to 6:5, expressed in terms of the molar ratio between the SiH content in the organohydrogenpolysiloxane and the total contents of terminal unsaturated groups in the organic compounds mixed.

The addition reaction for synthesizing silicone compounds represented by formula (9) can be performed under known conditions as in the case of silicone compounds represented by formula (1).

Further, compounds synthesized by addition reaction between hydrogenmethylsilicone compounds having branched structures in their main chains and polyoxyalkylene compounds of formula (14) and, if desired, polyoxyalkylene compounds of formula (13) can also be used as the silicone-branched polyether-modified silicones [B]. The compounds having branched structures in their main chains are synthesized by equilibration reaction using an acid catalyst under usual conditions. Therein, branched silicone units can be introduced by using trialkoxymethylsilane, trihydroxymethylsilane, tris(trimethylsiloxy)methylsilane, or a linear or cyclic polymer prepared from such a silane in the equilibration reaction.

However, the hydrogenmethylsilicones produced by the foregoing reaction is inconsistent in viscosity because their viscosities depend on residual silanol and alkoxy groups, and undergo an increase in viscosity with the lapse of time. Therefore, it is preferable to adopt equilibration reaction of a MT polymer (4) or a silicone compound of formula (7) with a silicone compound of formula (5) and/or a silicone compound of formula (6) in the presence of an acid catalyst. Although equilibration reaction can be carried out under the same conditions as mentioned above, it is appropriate that the catalyst used in the equilibration reaction be selected from acid catalysts. This is because at least one among $R^5$ and $R^6$ groups is a hydrogen atom and may cause dehydrogenation reaction when an acid catalyst is not used.

Synthesis examples of a MT polymer (4) and a silicone compound of formula (7) are described below.

Synthesis Example of MT Polymer

In a reaction vessel, 1,068 g of triethoxymethylsilane, 486 g of hexamethyldisiloxane and 486 g of isopropyl alcohol were placed, and thereto 10 g of methanesulfonic acid was added with stirring. Then, hydrolysis was carried out by dripping 216 g of water into the reaction vessel while cooling. Further, the reaction solution was ripened by heating at 70° C. for 2 hours, and then partially neutralized by adding thereto 8 g of a 49% water solution of NaOH, followed by completion of neutralization with 2 g of calcium carbonate. The reaction solution obtained was heated up to 140° C. under atmospheric pressure to remove the alcohol compounds, then cooled, and further filtered. The filtrate obtained was subjected to reduced-pressure distillation under a condition of 110° C./400 Pa to give 735 g (yield rate: 83%) of a MT polymer having a viscosity of 13 mm$^2$/s. By $^{29}$Si-NMR measurement of the MT polymer thus obtained, it was confirmed that the ratio of T units to M units in this polymer was 1.08 and the total contents of alkoxy and silanol groups in T units was 15 mole %.

Synthesis Example of 1,1,1,3,5,7,7,7-octamethyl-3, 5-dihydroxytetrasiloxane

In a reaction vessel, 200 g of water and 10 g of a 5% palladium-carbon catalyst were placed, and heated to 50° C. Thereto, 282 g of 1,1,1,3,5,7,7,7-octamethyltetrasiloxane was added dropwise. After ripening at 60° C. for 5 hours, the reaction mixture was cooled, and then filtered. The oil phase was separated from the filtrate, and then dried with anhydrous sodium sulfate. Thus, the intended 1,1,1,3,5,7,7,7-octamethyl-3,5-dihydroxytetrasiloxane was obtained in a yield of 250 g. This siloxane had a viscosity of 33 mm$^2$/s and a specific gravity of 0.988. In the $^{29}$Si-NMR measurement of this siloxane, the M unit-originated signal was observed at 8.3 ppm and the T unit-originated signal was observed at −56 ppm. The T/M value was 0.98 as determined on an integral basis.

The present silicone-branched silicone compounds can be used for various purposes. In particular, they are suitable for materials of all cosmetics applied to skin and hair. The appropriate proportion of a silicone compound (A) mixed in each cosmetic is from 0.1 to 80% by weight, and that of a silicone compound (B) in each cosmetic is from 0.1 to 40% by weight.

In addition to the silicone compounds mentioned above, the present cosmetic materials can contain unctuous agents (C) depending on the desired purposes thereof. The unctuous agents used therein may be in any of solid, semisolid and liquid states, provided that they have so far been used for general cosmetics. However, it is appropriate that at least a part of unctuous agents (C) added be in liquid state at room temperature.

More specifically, not only natural animal and vegetable fats and oils but also semi-synthetic fats and oils can be mixed in the present cosmetic materials, with examples including avocado oil, linseed oil, almond oil, Chinese wax, perilla oil, olive oil, cacao butter, kapok wax, kaya oil, carnauba wax, liver oil, candellila wax, beef tallow, beef foot oil, beef bone fat, hydrogenated beef tallow, apricot kernel oil, spermaceti, hydrogenated oil, wheat germ oil, sesame oil, rice germ oil, rice bran oil, sugar cane wax, sasanqua oil, safflower oil, shea butter, Chinese tung oil, cinnamon oil, jojoba wax, shellac wax, turtle oil, soybean oil, tea seed oil, tsubaki oil, evening primrose oil, corn oil, lard, rape seed oil, Japanese tung oil, rice-bran wax, germ oil, horse fat, persic oil, palm oil, palm kernel oil, castor oil, hydrogenated castor oil, methyl caster oil fatty acid, sunflower oil, grape seed oil, bayberry wax, jojoba oil, macadamia nut oil, beeds wax, mink oil, cottonseed oil, cotton wax, Japan wax, haze kernel oil, montan wax, coconut oil, hydrogenated coconut oil, tricoconut oil fatty acid glyceride, mutton-tallow, peanut oil, lanolin, liquid lanolin, reduced lanolin, lanolin alcohol, hard lanolin, lanolin acetate, lanolin fatty acid isopropyl, hexyl laurate, POE lanolin alcohol ether, POE lanolin alcohol acetate, polyethylene glycol lanolin fatty acid, POE hydrogenated lanolin alcohol ether, and egg yolk oil.

Examples of hydrocarbon oil which can be mixed include ozokerite, squalane, squalene, ceresine, paraffin, paraffin wax, liquid paraffin, pristane, polyisobutylene, microcrystalline wax and Vaseline; and examples of a higher fatty acid which can be mixed include lauric acid, myristic acid, palmitic acid, stearic acid, behenic acid, undecylenic acid, oleic acid, linoleic acid, linolenic acid, arachidonic acid, eicosapentaenoic acid (EPA), docosahexaenoic acid (DHA), isostearic acid and 12-hydroxystearic acid.

Examples of a higher alcohol which can be mixed include lauryl alcohol, myristyl alcohol, palmityl alcohol, stearyl alcohol, behenyl alcohol, hexadecyl alcohol, oleyl alcohol, isostearyl alcohol, hexyldodecanol, octyldodecanol, cetostearyl alcohol, 2-decyltetradecinol, cholesterol, phytosterol, POE cholesterol ether, monostearyl glycerin ether (batyl alcohol) and monooleyl glyceryl ether (cerakyl alcohol).

Examples of ester oil which can be mixed include diisobutyl adipate, 2-hexyldecyl adipate, di-2-heptylundecyl adipate, N-alkylglycol monoisostearates, isocetyl isostearate, trimethylolpropane triisostearic acid ester, ethylene glycol di-2-ethylhexanoic acid ester, cetyl 2-ethylhexanoate, trimethylolpropane tri-2-ethylhexanoic acid ester, pentaerythritol tetra-2-ethylhexanoic acid ester, cetyl octanoate, octyldodecyl gum ester, oleyl oleate, octyldodecyl oleate, decyl oleate, neopentyl glycol dicapric acid ester, triethyl citrate, 2-ethylhexyl cinnamate, amyl acetate, ethyl acetate, butyl acetate, isocetyl stearate, butyl stearate, diisopropyl sebacate, di-2-ethylhexyl sebacate, cetyl lactate, myristyl lactate, isopropyl palmitate, 2-ethylhexyl palmitate, 2-hexyldecyl palmitate, 2-heptylundecyl palmitate, cholesteryl 12-hydroxystearate, dipentaerythritol fatty acid esters, isopropyl myristate, octyldodecyl myristate, 2-hexyldecyl myristate, myristyl myristate, hexyldecyl dimethylocanoate, ethyl laurate, hexyl laurate, N-lauroyl-L-glutaminic acid 2-octyldodecyl ester and diisostearyl malic acid; and examples of glyceride oil which can be mixed include acetoglyceride, triisooctanoic acid glycride, triisostearic acid glyceride, triisopalmitic acid glyceride, monostearic acid glyceride, di-2-heptylundecanoic acid glyceride, trimyristic acid glyceride and myristic acid isostearic acid diglyceride.

As examples of silicone oils which can be mixed, mention may be made of organopolysiloxanes having from low to high viscosities, such as dimethylpolysiloxane, methylphenylpolysiloxane, methylhydrogenpolysiloxane and dimethylsiloxane-methylphenylsiloxane copolymer; cyclic siloxanes, such as octamethylcyclotetrasiloxane, decamethylcyclopentasiloxane, dodecamethylcyclohexasiloxane, tetramethyltetrahydrogencyclotetrasiloxane and tetramethyltetraphenylcyclotetrasiloxane; silicone rubbers, such as gummy dimethylpolysiloxanes having high polymerization degrees and gummy dimethylsiloxane-methylphenylsiloxane copolymers having high polymerization degrees; and cyclosiloxane solutions of silicone rubber, trimethylsiloxysilicate, cyclosiloxane solutions of trimethylsiloxysilicate, higher alkoxy-modified silicones such as stearoxysilicone, higher fatty acid-modified silicones, alkyl-modified silicones, amino-modified silicones, fluorine-modified silicones, and silicone resin solutions.

As examples of fluorine-containing oil which can be mixed, mention may be made of perfluoropolyether, perfluorodecalin and perfluorooctane.

Of those unctuous agents, silicone oils containing volatile silicones, unctuous agents having —[O—Si]$_n$— units in their molecular skeletons and unctuous agents having fluorine atoms or amino groups are preferred over the others.

In the present cosmetic materials, compounds (D) having at least one alcoholic hydroxyl group per molecule can be used in a proportion of at most 50.0 weight % depending on their desired purposes.

Examples of such alcohol compounds (D) which can be added include lower alcohol, such as ethanol or isopropanol; sugar alcohol, such as sorbitol or maltose; and sterols, such as cholesterol, sitosterol, phytosterol and lanosterol.

Examples of water-soluble polymers which can be added as compounds (D) include vegetable polymers, such as gum arabic, tragacanth, galactan, carob gum, guar gum, karaya gum, carrageenan, pectin, agar, quince seed, starch (rice, corn, potato, wheat), alge colloid, tranto gum and locust bean gum; microbial polymers, such as xanthan gum, dextran, succinoglucan and pullulan; animal polymers, such as collagen, casein, albumin and gelatin; starch polymers, such as carboxymethyl starch and methylhydroxypropyl starch; cellulose polymers, such as methyl cellulose, ethyl cellulose, methylhydroxypropyl cellulose, carboxymethyl cellulose, hydroxymethyl cellulose, hydroxypropyl cellulose, nitrocellulose, sodium cellulose sulfate, sodium carboxymethylcellulose, crystalline cellulose and powdery cellulose; alginic acid polymers, such as sodium alginate and propylene glycol ester of alginic acid; vinyl polymers, such as polyvinyl methyl ether and carboxyvinyl polymer; polyoxyethylene polymers; polyoxyethylene-polyoxypropylene copolymers; acrylic polymers, such as sodium polyacrylate, polyethylacrylate and polyacrylamide; other synthetic water-soluble polymers, such as polyethyleneimines and cationic polymers; and inorganic water-soluble polymers, such as bentonite, aluminum magnesium silicate, montmorillonite, beidellite, nontronite, saponite, hectorite and silicic acid anhydride.

In these water-soluble polymers, film-forming agents, such as polyvinyl alcohol and polyvinyl pyrrolidine, are also included.

Furthermore, the present cosmetic materials can contain powders (E) depending on the desired purposes. Such powders are not particularly restricted as to their shapes (whether they are spherical, acicular or tabular), their sizes (whether they are on the order of fume, fine grain or pigment), and their structures (whether they are porous or nonporous), provided that they have so far been used in traditional cosmetic materials. For instance, inorganic powders, organic powders, surfactant metal salt powders, colored pigments, pearl pigments, metallic powder pigments and natural colors can be added to the present cosmetic materials, if desired.

Examples of a usable inorganic powder include titanium dioxide, zirconium oxide, zinc oxide, cerium oxide, magnesium oxide, barium sulfate, calcium sulfate, magnesium sulfate, calcium carbonate, magnesium carbonate, talc, mica, kaolin, sericite, muscovite, synthetic mica, phlogopite, ruby mica, biotite, lipidolite, silicic acid, silicic acid anhydride, aluminum silicate, magnesium silicate, aluminum magnesium silicate, calcium silicate, barium silicate, strontium silicate, metal salts of tungstic acid, hydroxyapatite, vermiculite, haidilite, bentonite, montmorillonite, hectorite, zeolite, ceramics powder, calcium secondary phosphate, alumina, aluminum hydroxie, boron nitride and silica.

Examples of a usable organic powder include resin powders, such as polyamide powder, polyester powder, polyethylene powder, polypropylene powder, polystyrene powder, polyurethane powder, benzoguanamine powder, polymethyl benzoguanamine powder, poly(tetrafluoroethylene) powder, polymethyl methacrylate powder, cellulose powder, silk powder, nylon powder (e.g., 12-nylon powder or 6-nylon powder), silicone elastomer powder, styrene-acrylic acid copolymer powder, divinylbenzene-styrene copolymer powder, vinyl resin powder, urea resin powder, phenol resin powder, fluororesin powder, silicone resin powder, acrylic resin powder, melamine resin powder, epoxy resin powder and polycarbonate resin powder; microcrystalline fiber powder; starch powder; and lauroyl lysine powder. In addition, organic powders comprising —[Si—O]$_n$— units in their molecular skeletons can be used to advantage.

Examples of a usable surfactant metal salt powder (metal soap powder) include powders of zinc stearate, aluminum stearate, calcium stearate, magnesium stearate, zinc myristate, magensium myristate, zinc cetylphosphate, calcium cetylphosphate and zinc sodium cetylphosphate.

Examples of a usable colored pigment include inorganic red pigments, such as iron oxide, iron hydroxide and iron titanate; inorganic brown pigments, such as γ-iron oxide; inorganic yellow pigments, such as iron oxide yellow and loess; inorganic black pigments, such as iron oxide black and carbon black; inorganic violet pigments, such as manganese violet and cobalt violet; inorganic green pigments, such as chromium hydroxide, chromium oxide, cobalt oxide and cobalt titanate; inorganic blue pigments, such as Prussian blue and ultramarine blue; lakes of tar pigments; lakes of natural dyes; and synthetic resin powder complexes of the inorganic pigments as recited above.

Examples of a usable pearl pigment include titanium oxide-coated mica, bismuth oxychloride, titanium oxide-coated bismuth oxychloride, titanium oxide-coated talc, fish scales, and titanium oxide-coated colored mica; and examples of a usable metallic powder pigment include aluminum powder, copper powder and stainless powder.

The tar pigments described above include Red No. 3, Red No. 104, Red No. 106, Red No. 201, Red No. 202, Red No. 204, Red No. 205, Red No. 220, Red No. 226, Red No. 227, Red No. 228, Red No. 230, Red No. 401, Red No. 505, Yellow No. 4, Yellow No. 5, Yellow No. 202, Yellow No. 203, Yellow No. 204, Yellow No. 401, Blue No. 1, Blue No. 2, Blue No. 201, Blue No. 404, Green No. 3, Green No. 201, Green No. 204, Green No. 205, Orange No. 201, Orange No. 203, Orange No. 204, Orange No. 206 and Orange No. 207 (according to the pigment nomenclature method in JIS); and the natural pigments described above include powders of carminic acid, laccaic acid, carthamin, bradilin and crocin.

Additionally, complexes of the powders as recited above or those obtained by treating the powders as recited above with general unctuous agents, silicone oil, a fluorine-containing compound or a surfactant may be used. Also, the powders as recited above may be used as a mixture of two or more thereof, if desired.

Besides containing the present silicone compounds (B), the present cosmetic materials may contain known surfactants (F) depending on the desired purposes. Such additional surfactants have no particular restrictions, but they may be any of anionic, cationic, nonionic and amphoteric ones so long as they have hitherto been used in general cosmetics.

Examples of a usable anionic surfactant include fatty acid soap, such as sodium stearate or triethanolamine palmitate; alkyl ether carboxylic acids and salts thereof; salts of amino acid-fatty acid condensates; alkanesulfonates; alkenesulfonates; sulfonated fatty acid esters; sulfonated fatty acid amides; sulfonates of formaldehyde condensate type; alkylsulfates; higher secondary alcohol sulfates; alkyl and aryl ether sulfates; fatty acid ether sulfates, fatty acid alkylolamide sulfates; ether sulfates, such as Turkeky red oil; alkyl phosphates; ether phosphates; alkyl aryl ether phosphates; amide phosphates; and active agents of N-acylamino acid type.

Examples of a usable cationic surfactant include amine salts, such as alkylamine salts, polyamines and aminoalcohol fatty acid derivatives, quaternary alkylammonium salts, quaternary arylammonium salts, pyridinium salts and imidazolium salts.

Examples of a usable nonionic surfactant include sorbitan fatty acid esters, glycerin fatty acid esters, polyglycerin fatty acid esters, propylene glycol fatty acid esters, polyethylene glycol fatty acid esters, sucrose fatty acid esters, polyoxyethylene alkyl ethers, polyoxypropylene alkyl ethers, polyoxyethylene alkyl phenyl ethers, polyoxyethylene fatty acid esters, polyoxyethylene sorbitan fatty acid esters, polyoxyethylene sorbitol fatty acid esters, polyoxyethylene glycerin fatty acid esters, polyoxyethylene propylene glycol fatty acid esters, polyoxyethylene castor oil, polyoxyethylene hydrogenated castor oil, polyoxyethylene phytostanol ether, polyoxyethylene phytosterol ether, polyoxyethylene cholestanol ether, polyoxyethylene cholesteryl ether, polyoxyalkylene-modified organopolysiloxanes, organopolysiloxanes modified with both polyoxyalkylene and alkyl groups, alkanolamides, sugar ethers and sugar amides; and examples of a usable amphoteric surfactant include betaine, aminocarboxylic acid salts and imdazoline derivatives.

Furthermore, the present cosmetic materials may contain cross-linked organopolysiloxanes (G), if desired. The cross-linked organopolysiloxanes suitable for addition to the present cosmetic materials are those which cause swelling when they contain a silicone having low viscosity of from 0.65 to 10.0 mm$^2$/sec (25°) in a quantity larger than the weight of the cross-linked organopolysiloxanes themselves. And it is preferable that the cross-linked structure of those organopolysiloxanes be formed by the reaction between the hydrogen atoms bonded directly to silicon atoms and a cross-linking agent having at least two vinylic reactive moieties per molecule. In the cross-linking reaction, it is appropriate to use the cross-linking agent containing at least one moiety selected from polyoxyalkylene, alkyl, alkenyl, aryl or fluoroalkyl moieties. The suitable proportion of such cross-linked organopolysiloxanes mixed in the present cosmetic material is from 0.1 to 30.0 weight %, preferably from 1.0 to 10.0 weight %, to the total weight of the cosmetic material.

The present cosmetic material can further contain one or more of silicone resins (H), such as acryl-silicone graft or block copolymers and silicone compounds having a reticular structure, if needed.

In particular, acrylsilicone resins are suitable for the present cosmetic materials. Further, it is desirable that at least one moiety selected from the group consisting of pyrrolidone, long-chain alkyl, polyoxyalkylene and fluoroalkyl moieties be present in such an acrylsilicone resin molecule. Further, it is appropriate for those silicone resins to be reticular silicone compounds. When the silicone resins, such as acryl-silicone graft or block copolymer and silicone compounds having a reticular structure, are mixed in the present cosmetic material, the appropriate proportion of silicone resins mixed is from 0.1 to 20 weight %, preferably from 1 to 10 weight %, to the total weight of the cosmetic material.

To the present cosmetic materials, the agents used in general cosmetic materials, such as water, an oil-soluble gelling agent, clay minerals modified with organic compounds, resins, ultraviolet absorbents, a moisture retention agent, antiseptics, an antimicrobial agent, perfume, salts, antioxidants, pH regulators, a chelating agent, refrigerant, an anti-inflammatory agent, skin beautifying components (a skin whitener, a cell activator, a rough dry skin improver, a blood circulation promoter, a skin astringent and an anti-seborrheic agent), vitamins, amino acids, nucleic acids, hormones and clathrate compounds, can be added so far as they have no adverse influence on the effects of the present invention.

Examples of an oil-soluble gelling agent which can be added include metal soaps, such as aluminum stearate, magnesium stearate and zinc myristate; amino acid derivatives, such as N-lauroyl-L-glutamic acid and $\alpha,\gamma$-di-n-butylamine; dextrin fatty acid esters, such as dextrin palmitic acid ester, dextrin stearic acid ester and dextrin 2-ethylhexaminic acid palmitic acid ester; sucrose fatty acid esters, such as sucrose palmitic acid ester and sucrose stearic acid ester; benzylidene derivatives of sorbitol, such as monobenzylidene sorbitol and dibenzylidene sorbitol; and clay minerals modified with organic compounds, such as dimethylbenzyldodecyl ammonium montmorillonite clay and dimethyldioctadecyl ammonium montmorillonite clay.

Examples of an ultraviolet absorbent which can be added include ultraviolet absorbents of benzoic acid type, such as p-aminobenzoic acid; those of anthranilic acid type, such as methyl anthranilate; those of salicylic acid type, such as methyl salicylate; those of succinic acid type, such as octyl p-methoxysuccinate; those of benzophenone type, such as 2,4-dihydroxybenzophenone; those of urocanic acid type, such as ethyl urocanate; and those of dibenzoylmethane type, such as 4-t-butyl-4'-methoxydibenzoylmethane.

Examples of a moisture retention agent which can be added include glycerin, sorbitol, propylene glycol, dipropylene glycol, 1,3-butylene glycol, glucose, xylitol, maltitol, polyethylene glycol, hyaluromic acid, chondroitin sulfuric acid, pyrrolidone carboxylate, polyoxyethylene glycoside, and polyoxypropylene methylglycoside.

Examples of an antiseptic agent which can be added include alkyl p-hydroxybenzoates, benzoic acid, sodium benzoate, sorbic acid, potassium sorbate and phenoxyethanol; and examples of an antimicrobial agent which can be added include benzoic acid, salicylic acid, carbolic acid, sorbic acid, alkyl p-hydroxybenzoates, p-chlorometacresol, hexachlorophene, benzalkonium chloride, chlorhexidine chloride, trichlorocarbanilide, photosensitizers and phenoxyethanol.

Examples of an antioxidant which can be added include tocopherol, butylhydroxyanisole, dibutylhydroxytoluene and phytic acid; examples of a pH regulator which can be added include lactic acid, citric acid, glycolic acid, succinic acid, tartaric acid, dl-malic acid, potassium carbonate, sodium hydrogen carbonate and ammonium hydrogen carbonate; examples of a chelating agent which can be added include alanine, sodium ethylenediaminetetraacetate, sodium polyphosphate, sodium metaphosphate and phosphoric acid; examples of a refrigerant which can be added include L-menthol and camphor; and examples of an anti-inflammatory agent which can added include allantoin, glycyrrhizin and salts thereof, glycyrrhetinic acid and stearyl glycyrrhetinate, tranexamic acid and azulene.

Examples of a skin-beautifying component which can be added include whitening agents, such as placenta extract, arbutin, glutathione and Yukinoshita extract; cell activators, such as royal jelly, photosensitizers, cholesterol derivatives and calf blood extract; rough dry skin improvers; blood circulation improvers, such as nonylic acid vanillyl amide, benzyl nicotinate, β-butoxyethyl nicotinate, capsaicin, zingerone, cantharis tincture, ichtammol, caffeine, tannic acid, α-borneol, tocopheryl nicotinate, inositol hexanicotinate, cyclandelate, cinnarizine, tolazoline, acetyl choline, verapamil, cepharanthin and γ-oryzanol; skin astringents, such as zinc oxide and tannic acid; and antiseborrheic agents, such as sulfur and thianthol.

Examples of vitamins which can be added include vitamin A, such as vitamin A oil, retinol, retinyl acetate and retinyl palmitate; vitamin B, including vitamin $B_2$ such as riboflavin, riboflavin butyrate and flavin adenine nucleotide, vitamin $B_6$ such as pyridoxine hydrochloride, pyridoxine dioctanoate and pyridoxine tripalmitate, vitamin $B_{12}$ and its derivatives, and vitamin $B_{15}$ and its derivatives; vitamin C, such as L-ascorbic acid, L-ascorbic acid dipalmitic ester, sodium (L-ascorbic acid)-2-sulfate and dipotassium L-ascorbic acid diphosphate; vitamin D, such as ergocalciferol and cholecarciferol; vitamin E, such as α-tocopherol, β-tocopherol, γ-tocopherol, dl-α-tocopheryl acetate, dl-α-tocopheryl nicotinate and dl-α-tocopheryl succinate; vitamin H; vitamin P; nicotinic acids, such as nicotinic acid, benzyl nicotinate and nicotinic acid amide; pantothenic acids, such as calcium pantothenate, D-pantothenyl alcohol, pantothenyl ethyl ether and acetylpantothenyl ethyl ether; and biotin.

Examples of an amino acid which can be added include glycine, valine, leucine, isoleucine, serine, threonine, phenylaranine, alginine, lysine, aspartic acid, glutamic acid, cystine, cysteine, methionine, and tryptophan; examples of a nucleic acid which can be added include deoxyribonucleic acid; and examples of hormone which can be added include estradiol and ethenyl estradiol.

The term "cosmetic materials" as used herein are intended to include skin care products, such as face lotion, milky lotion, cream, face cleansing cream, massage materials, toilet soap and detergent, antiperspirant and deodorant; makeup products, such as face powder, foundation, rouge, eye shadow, mascara, eyeliner and lipstick; and hairdressing products, such as shampoo, rinse and treatment.

Additionally, the present cosmetic materials may have any of forms, including liquid, emulsion, solid, paste, gel and spray forms, if desired.

The present invention will now be illustrated in greater detail by reference to the following examples. However, the invention should not be construed as being limited to these examples. And the term "%" used hereinafter means "% by weight" unless otherwise noted.

Additionally, the entire disclosure of all applications, patents and publications, cited above and below, and of corresponding Japanese application No. 2000-375585, filed on Dec. 11, 2000, is hereby incorporated by reference.

SYNTHESIS EXAMPLE 1

In a reaction vessel, 268 parts by weight of a cyclic siloxane represented by the following structural formula (16) and 300 parts by weight of toluene were placed, and then mixed with 0.2 parts by weight of a 2% toluene solution of chloroplatinic acid. Thereto, 348 parts by weight of pentamethylvinyldisiloxane was added dropwise while refluxing the solvent, thereby running reaction between those siloxanes.

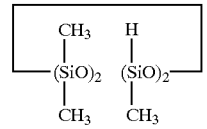

(16)

Then, the reaction mixture was heated under reduced pressure to distill off the solvent therefrom. Thus, organopolysiloxane having the following structural formula (17) were obtained.

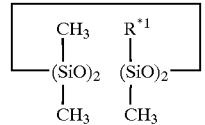

(17)

wherein —$R^{*1}$ is $R^{*1}$ = —$C_2H_4SiOSi(CH_3)_3$ with $CH_3$ groups

The product obtained was a colorless transparent liquid, and it had a viscosity of 12 mm²/s (at 25° C.) and a specific gravity of 0.930 (at 25° C.).

SYNTHESIS EXAMPLE 2

In a reaction vessel, 56 parts by weight of organohydrogensiloxane represented by the following structural formula (18) was mixed with 2 parts by weight of a 0.5% toluene solution of chloroplatinic acid. Further thereto, 310 parts by weight of organopolysiloxane represented by the following structural formula (19) were added dropwise and underwent reaction with the organohydrogensiloxane at 80° C. for 6 hours.

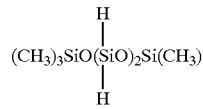

(18)

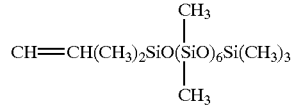

(19)

Then, the reaction mixture was heated under reduced pressure to distill off low boiling substances therefrom. Thus, organopolysiloxane having the following structural formula (20) were obtained.

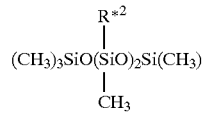

(20)

wherein —$R^{*2}$ is $R^{*2}$ = —$C_2H_4(CH_3)_2SiO(SiO)_6Si(CH_3)_3$ with $CH_3$ groups The product obtained was a colorless transparent liquid, and it had a viscosity of 18 mm²/s (at 25° C.) and a specific gravity of 0.934 (at 25° C.).

SYNTHESIS EXAMPLE 3

After 715 parts by weight of organohydrogenpolysiloxane represented by the following structural formula (21) and 700 parts by weight of toluene were placed in a reaction vessel, 2 parts by weight of a 0.5% toluene solution of chloroplatinic acid was added thereto, and further thereto 174 parts by weight of pentamethylvinyldisiloxane was added dropwise while refluxing the solvent, thereby running reaction between those siloxanes.

To the resulting reaction mixture, 252 parts by weight of 1-hexene was added dropwise, and the reaction was further continued for 6 hours.

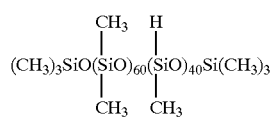
(21)

Then, the reaction mixture was heated under reduced pressure to distill off the solvent therefrom. Thus, organopolysiloxane having the following structural formula (22) were obtained.

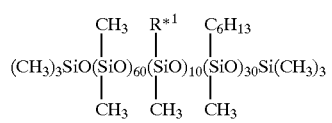
(22)

The product obtained was a colorless transparent liquid, and it had a viscosity of 500 mm$^2$/s (at 25° C.) and a specific gravity of 0.945 (at 25° C.).

SYNTHESIS EXAMPLE 4

In a reaction vessel, 409 parts by weight of organohydrogensiloxane represented by the following structural formula (23) and 490 parts by weight of toluene were placed, and thereto 2 parts by weight of a 0.5% toluene solution of chloroplatinic acid was added. Further thereto, 530 parts by weight of pentamethylvinyldisiloxane was added dropwise and underwent reaction with the organohydrogensiloxane for 6 hours under reflux of the solvent.

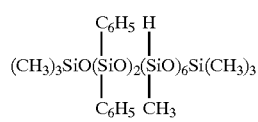
(23)

Then, the reaction mixture was heated under reduced pressure to distill off the solvent therefrom. Thus, organopolysiloxane having the following structural formula (24) were obtained.

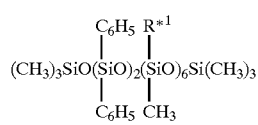
(24)

The product obtained was a colorless transparent liquid, and it had a viscosity of 230 mm$^2$/s (at 25° C.) and a specific gravity of 0.977 (at 25° C.)

SYNTHESIS EXAMPLE 5

After 546 parts by weight of organohydrogenpolysiloxane represented by the following structural formula (25) and 360 parts by weight of toluene were placed in a reaction vessel, 0.2 parts by weight of a 2% toluene solution of chloroplatinic acid was added thereto.

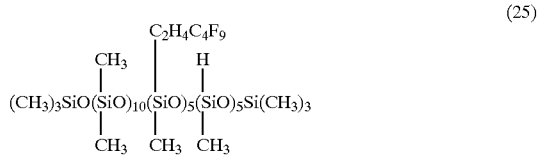
(25)

Further thereto, 174 parts by weight of pentamethylvinyldisiloxane was added dropwise and underwent reaction with the organohydrogensiloxane under reflux of the solvent. The reaction mixture was heated under reduced pressure to distill off the solvent therefrom. Thus, organopolysiloxane having the following structural formula (26) were obtained.

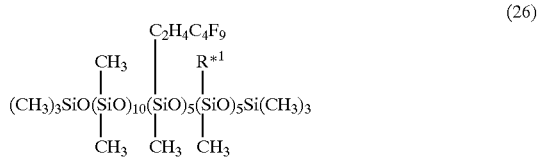
(26)

The product obtained was a colorless transparent liquid, and it had a viscosity of 113 mm$^2$/s (at 25° C.) and a specific gravity of 1.126 (at 25° C.).

SYNTHESIS EXAMPLE 6

In a reaction vessel, 200 parts by weight of methylvinylpolysiloxane having a vinyl value of 0.135 mole/100 g, 920 parts by weight of organopolysiloxane having the following structural formula (27) and 1,000 parts by weight of toluene were placed, and thereto 2 parts by weight of a 0.5% toluene solution of chloroplatinic acid was added. Therein, reaction was run for 6 hours under reflux of the solvent.

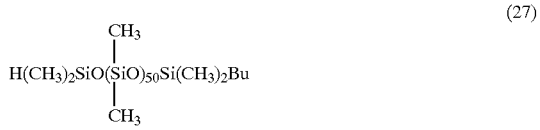
(27)

Then, the reaction mixture was heated under reduced pressure to distill off the solvent therefrom. The organopolysiloxane thus obtained was a colorless transparent liquid and had a viscosity of 1,800 mm$^2$/s (at 25° C.) and a specific gravity of 0.968 (at 25° C.).

SYNTHESIS EXAMPLE 7

In a reaction vessel, 480 parts by weight of organohydrogenpolysiloxane represented by the following structural formula (28) and 1,000 parts by weight of toluene were placed, and thereto 0.2 parts by weight of a 2% toluene solution of chloroplatinic acid was added.

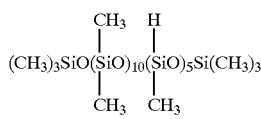

(28)

Further thereto, 600 parts by weight of the organopolysiloxane of the foregoing structural formula (19) was added dropwise and underwent reaction with the organohydrogenpolysiloxane while refluxing the solvent for 2 hours. Furthermore, 780 parts by weight of a 50% toluene solution of allyl stearate was added dropwise thereto, and underwent reaction for 3 hours.

Then, the reaction mixture was heated under reduced pressure to distill off the solvent therefrom. Thus, organopolysiloxane having the following structural formula (29) were obtained.

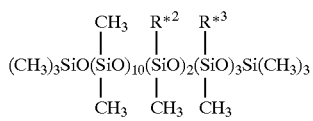

(29)

wherein ——R*³ stands for ——C₃H₆OC(═O)C₁₇H₃₅.

The product obtained was a colorless transparent liquid, and it had a viscosity of 70 mm²/s (at 25° C.) and a specific gravity of 0.947 (at 25° C.).

SYNTHESIS EXAMPLE 8

In a reaction vessel, 148 g of an MT polymer, 16 g of hexamethyldisiloxane and 585 g of octamethylcyclotetrasiloxane were placed, and thereto 0.02 g of potassium hydroxide was added. Therein, equilibration reaction was run at 145° C. for 3 hours. After cooling down to 80° C., the reaction solution was neutralized by addition of 0.1 g of ethylene chlorohydrin, and the salt was removed therefrom by pressurized filtration. The filtrate obtained was distilled under reduced pressure (around 240°/400 Pa) to yield 680 g of a branched polysiloxane oil having a viscosity of 102 mm²/s at 25° C. The yield rate was 90%. The branched polysiloxane oil obtained caused neither gelling during the distillation under reduced pressure nor any change in appearance with the lapse of time. From the structural analysis by ²⁹Si-NMR measurement, this product was found to have a M/T/D ratio of 1/9.2/1.3.

SYNTHESIS EXAMPLE 9

In a reaction vessel, 315 g of 1,1,1,3,5,7,7,7-octamethyl-3,5-dihydroxytetrasiloxane and 310 g of decamethyltetrasiloxane were placed. Thereto, 1.9 g of 97% sulfuric acid was added as an acid catalyst, and the contents in the reaction vessel were stirred for 1 hour at room temperature. The reaction mixture was further admixed with 16.9 g of 97% sulfuric acid and stirred for 4 hours at room temperature. Then, 9.4 g of water was added thereto, and stirred for 1 hour at room temperature. Thereafter, the waste acid was separated. The resulting reaction mixture was washed with water, and then checked for neutrality with pH test paper, and further subjected to pressurized filtration. Thus, a branched polysiloxane oil having a viscosity of 22 mm²/s at 25° C. was obtained. Further, this oil was subjected to distillation under reduced pressure (1300 Pa), and a fraction distilled at temperatures from 140 to 180° C. was taken. This fraction of the branched polysiloxane oil had a viscosity of 8 mm²/s at 25° C., and caused neither gelling during the distillation under reduced pressure nor any change in appearance with the lapse of time. From the structural analysis by ²⁹Si-NMR measurement, this product was found to have a M/T/D ratio of 1/0.7/0.8.

SYNTHESIS EXAMPLE 10

In a reaction vessel, 315 g of 1,1,1,3,5,7,7,7-octamethyl-3,5-dihydroxytetrasiloxane, 1184 g of hexamenthylcyclotrisiloxane and 300 g of acetonitrile were placed, subjected to ring-opening polymerization at 55° C. in the presence of a five-coordinate silicon complex catalyst, ripened for 2 hours, and then cooled. Thereto, 444 g of triethyl ammonium was added, and further 436 g of trimethylchlorosilane was added dropwise at a slow speed to cease the reaction. The resulting reaction mixture was washed with water, and then checked for neutrality with pH test paper, and further subjected to pressurized filtration. The filtrate thus obtained was subjected to distillation at 110° C. under reduced pressure of 1300 Pa to give 1,420 g of a branched polysiloxane oil having a viscosity of 20 mm²/s at 25° C. The yield was 86%. The branched polysiloxane oil caused neither gelling during the distillation under reduced pressure nor any change in appearance with the lapse of time. From the structural analysis by ²⁹Si-NMR measurement, this product was found to have a M/T/D ratio of 1/0.5/3.3.

SYNTHESIS EXAMPLE 11

In a reaction vessel, 1,000 parts by weight of the silicone-grafted polysiloxane prepared in Synthesis Example 6 and 200 parts by weight of organopolysiloxane gum were placed, and stirred to prepare a silicone gum solution having a viscosity of 40,000 mPa·s.

SYNTHESIS EXAMPLE 12

In a reaction vessel, 700 parts by weight of a toluene solution of silicone resin having a weight average molecular weight of 4,700 (resin concentration: 72%) and 520 parts by weight of the silicone-grafted polysiloxane prepared in Synthesis Example 9 were placed. Then, the reaction vessel was heated to raise an inside temperature thereof to 120° C., and the toluene was removed by distillation under reduced pressure. Further, the inside temperature was raised to 130° C., and 30 parts by weight of the silicone-grafted polysiloxane was distilled away and the toluene was removed completely. After filtration, the volatile component in the filtrate was adjusted, and 50% of a siloxane solution of silicone resin was obtained in an amount of 1,000 parts by weight.

SYNTHESIS EXAMPLE 13

In a reaction vessel, 74 g of an MT polymer, 1.6 g of hexamethyldisiloxane, 925 g of octamethylcyclotetrasiloxane and 6 g of an aminopolysiloxane of the following formula (30) were placed, and thereto 0.2 g of potassium hydroxide was added. Therein, equilibration reaction was run at 145° C. for 3 hours.

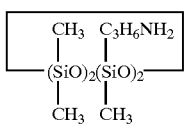
(30)

After cooling to 80° C., the reaction mixture was neutralized by addition of 0.6 g of ethylene chlorohydrin, and the salt produced was removed by filtration under reduced pressure. The filtrate thus obtained was subjected to distillation at temperatures around 150° C. under reduced pressure of 400 Pa to give 855 g of a branched polysiloxane oil having a viscosity of 12,000 mPa·s at 25° C. and an amine equivalent of 19,500 g/mole. The yield was 85%. The branched polysiloxane oil caused neither gelling during the distillation under reduced pressure nor any change in appearance with the lapse of time. From the structural analysis by $^{29}$Si-NMR measurement, this product was found to have a M/T/D ratio of 1/0.9/25.

SYNTHESIS EXAMPLE 14

In a reaction vessel, 714 parts by weight of organohydrogenpolysiloxane represented by the following structural formula (31), 270 parts by weight of organopolysiloxane represented by the foregoing structural formula (19) and 638 parts by weight of toluene were mixed, and thereto 2 parts by weight of a 0.5 weight % isopropyl alcohol solution of chloroplainic acid was added. The resultant mixture underwent reaction for 6 hours while refluxing the solvent.

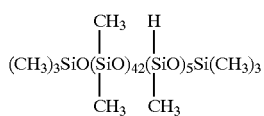
(31)

Thereto, 291 parts by weight of polyoxyalkylene represented by the following structural formula (32) was further added and reaction was continued.

$$CH_2=CHCH_2O(C_2H_4O)_9H \qquad (32)$$

After continuing the reaction for 6 hours under reflux of the solvent, the reaction solution was heated under reduced pressure to distill off the solvent therefrom, and then admixed with 200 parts of ethanol. Thereto, 7.1 parts by weight of a 5% aqueous solution of sodium hydroxide was added to hydrolyze Si—H groups remaining unreacted, followed by neutralization with 0.9 parts by weight of concentrated hydrochloric acid.

Furthermore, 147 parts by weight of a 0.01N aqueous solution of hydrogen chloride was added to hydrolyze ally ether groups of polyoxyalkylene remaining unreacted, and neutralization was carried out with 2.5 parts by weight of a 5% aqueous sodium bicarbonate. The reaction solution was heated under reduced pressure to distill off the solvent therefrom, and subjected to filtration. Thus, organopolysiloxane represented by the following structural formula (33) were obtained.

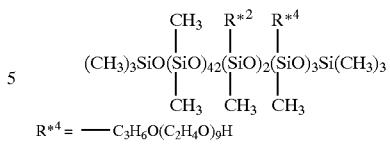
(33)

This product was a colorless transparent liquid having a viscosity of 956 mm$^2$/s at 25° C. and a specific gravity of 1.002 (25° C.)

SYNTHESIS EXAMPLE 15

In a reaction vessel, 838 parts by weight of organohydrogenpolysiloxane represented by the following structural formula (34) and 600 parts by weight of isopropyl alcohol were placed, and thereto 0.2 parts by weight of a 2 weight % isopropyl alcohol solution of chloroplatinic acid was added.

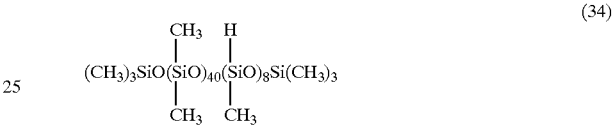
(34)

Thereto, 338 parts by weight of the organopolysiloxane of the foregoing structural formula (19) was added dropwise and reacted with the organohydrogenpolysiloxane while refluxing the solvent for 3 hours.

Further thereto, 424 parts by weight of oleylpolyoxypropylene (3) allyl ether (RG-1252 produced by Sanyo chemical Industries Ltd.) was added dropwise, and reaction was completed by 3-hour heating under reflux. Then, the reaction mixture was mixed with 8.4 parts by weight of a 5% aqueous solution of sodium hydroxide to hydrolyze Si—H groups remaining unreacted, followed by neutralization with 1.1 parts by weight of concentrated hydrochloric acid. Furthermore, 255 parts by weight of a 0.01 N aqueous solution of hydrogen chloride was added to hydrolyze unreacted ally ether groups, and neutralization was carried out with 4.3 parts by weight of a 5% aqueous sodium bicarbonate. The reaction solution was heated under reduced pressure to distill off the solvent therefrom, and subjected to filtration. Thus, organopolysiloxane represented by the following structural formula (35) were obtained.

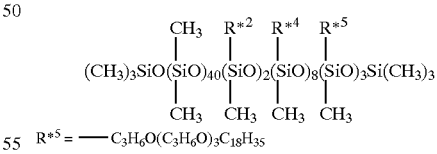
(35)

This product was a light brown transparent liquid having a viscosity of 340 mm$^2$/s at 25° C. and a specific gravity of 0.981 (25° C.)

SYNTHESIS EXAMPLE 16

In a reaction vessel, 380 parts by weight of the polyoxyalkylene represented by the foregoing structural formula (32), 222 parts by weight of the organopolysiloxane represented by the following structural formula (36) and 600 parts by weight of isopropyl alcohol were mixed, and thereto 0.2 parts by weight of a 2 weight % isopropyl alcohol solution of chloroplatinic acid was added.

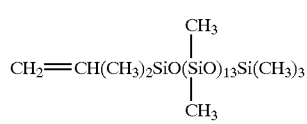

(36)

To the admixture under reflux, 546 parts by weight of organohydrogenpolysiloxane represented by the following structural formula (37) was further added dropwise, thereby conducting reaction therein.

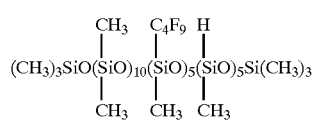

(37)

Thereto, 5.5 parts by weight of a 5% aqueous solution of sodium hydroxide was added to hydrolyze Si—H groups remaining unreacted, followed by neutralization with 0.7 parts by weight of concentrated hydrochloric acid. Further, 175 parts by weight of a 0.01N aqueous solution of hydrogen chloride was added to hydrolyze ally ether groups of polyoxyalkylene remaining unreacted, and neutralization was carried out with 2.9 parts by weight of a 5% aqueous sodium bicarbonate. The reaction solution was heated under reduced pressure to distill off the solvent therefrom. Thus, organopolysiloxane represented by the following structural formula (38) was obtained.

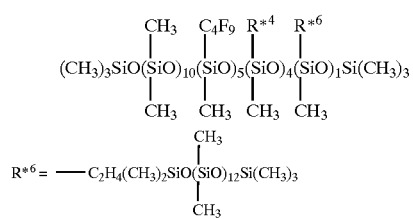

(38)

This product was a colorless transparent liquid having a viscosity of 910 mm$^2$/s at 25° C. and a specific gravity of 1.131 (25° C.)

SYNTHESIS EXAMPLE 17

In a reaction vessel, 148 g of an MT polymer, 48 g of dodecamethylpentasiloxane, 134 g of hexadecamethyldecasiloxane and 74 g of octamethylcyclotetrasiloxane were placed, and thereto 12.0 g of concentrated sulfuric acid was added. Therein, equilibration reaction was run for 5 hours at room temperature. After waste acid was separated, the reaction mixture was washed with water for neutralization. The resultant reaction mixture was distilled under reduced pressure (around 110° C./400 Pa) to give 280 g of a branched polysiloxane oil having a viscosity of 20 mm$^2$/g and a specific gravity of 0.994 at 25° C. This branched polysiloxane oil caused neither gelling during the distillation under reduced pressure nor any change in appearance with the lapse of time. From the structural analysis by $^{29}$Si-NMR measurement, this product was found to have a M/T/(D+DH) ratio of 1/1.1/2.8.

A 92 g portion of this silicone-branched methylhydrogenpolysiloxane, 284 g of polyethylene glycol (10) allyl methyl ether and 200 g of isopropyl alcohol were placed in a reaction vessel, and thereto 0.5 g of a 5% isopropyl alcohol solution of chloroplatinic acid was added. Therein, reaction was run for 5 hours at 80° C. Further, 38 g of 0.01 N aqueous hydrochloric acid solution was added and hydrolysis was carried out for 3 hours at 60° C. Thereafter, 1.0 g of 5% aqueous sodium bicarbonate was added for neutralization. The reaction solution obtained was distilled under reduced pressure (around 110° C./400 Pa), and then filtered. Thus, 320 g of water-soluble branched polysiloxane oil having a viscosity of 250 mm$^2$/s at 25° C. and a refractive index of 1.4530 was obtained. The yield was 85%.

SYNTHESIS EXAMPLE 18

In a reaction vessel, 31.5 g of 1,1,1,3,5,7,7,7-octamethyl-3,5-dihydroxytetrasiloxane, 350 g of octamethyltetrasiloxane, 18 g of tetramethylcyclotetrasiloxane and 97.6 g of permethyldodecasiloxane were placed. Thereto, 1.53 g of 97% sulfuric acid was added as an acid catalyst, and the contents in the reaction vessel were stirred for 1 hour at room temperature. The reaction mixture was further admixed with 13.3 g of 97% sulfuric acid and stirred for 4 hours at room temperature. Then, 7.4 g of water was added thereto, and stirred for 1 hour at room temperature. Thereafter, the waste acid was separated. The resulting reaction mixture was washed with water, and then checked for neutrality with pH test paper, and further subjected to pressurized filtration. The filtrate was distilled under reduced pressure (around 110° C./400 Pa). Thus, a silicone-branched methylhydrogenpolysiloxane having a viscosity of 38 mm$^2$/s at 25° C. was obtained. This branched polysiloxane caused neither gelling during the distillation under reduced pressure nor any change in appearance with the lapse of time, and had a weight average molecular weight of 4,700 on a polystyrene basis as measured by GPC. Further, this product was found to have a M/T/D ratio of 1/0.5/11.5 from the structural analysis by $^{29}$Si-NMR measurement.

A 470 g portion of the silicone-branched methylhydrogenpolysiloxane, 150 g of polyethylene glycol (9) allyl ether and 400 g of isopropyl alcohol were placed in a reaction vessel, and thereto 0.3 g of a 3% isopropyl alcohol solution of chloroplatinic acid was added. In the reaction vessel, reaction was run for 5 hours at 80° C. The reaction solution thus obtained was transferred into an autoclave, and thereto 10 g of 5% palladium-carbon catalyst was added. Further, hydrogen was admitted into the autoclave. Therein, reaction was run for 3 hours at room temperature. During the reaction, the hydrogen pressure was kept at 1 MPa. The catalysts were removed by filtration, and the filtrate obtained was distilled under reduced pressure (around 110° C./400 Pa) to give 680 g of branched polysiloxane oil having a viscosity of 330 mm$^2$/s and a refractive index of 1.4195 at 25° C.). The yield was 90%.

Evaluation of Emulsification Stability

Emulsions having the following compositions were prepared.

| Ingredients | Comparative Examples | | | Examples | | |
|---|---|---|---|---|---|---|
| | 1 | 2 | 3 | 1 | 2 | 3 |
| KF-96A-20 | 20 | — | — | — | — | — |
| Silicone compound prepared in Synthesis Example 2 | — | 20 | — | 20 | 20 | — |

-continued

| Ingredients | Comparative Examples | | | Examples | | |
|---|---|---|---|---|---|---|
| | 1 | 2 | 3 | 1 | 2 | 3 |
| Silicone compound prepared in Synthesis Example 10 | — | — | 20 | — | — | 20 |
| KF-6017 | 2 | 2 | 2 | — | — | — |
| Silicone compound prepared in Synthesis Example 14 | — | — | — | 2 | — | 2 |
| Silicone compound prepared in Synthesis Example 18 | — | — | — | — | 2 | — |
| NaCl | 1 | 1 | 1 | 1 | 1 | 1 |
| Purified water | 77 | 77 | 77 | 77 | 77 | 77 |

KF-96A-20 is dimethicone (viscosity: 20 mm$^2$/s), or dimethylpolysiloxane produced by Shin-Etsu Chemical Co., Ltd.

KF-6017 is a polyether-modified silicone (HLB=5) produced by Shin-Etsu Chemical Co., Ltd.

Additionally, the proportion of each ingredient in the table is expressed in weight %.

The emulsions prepared were stored in a 50° C. constant temperature bath, and each of them was examined for change in rotational viscosity with the passage of time. Rates of viscosity changes caused in each emulsion with the passage of time are set forth in the following table in terms of the relative viscosity, or the ratio of a rotational viscosity after a lapse of specified days ($\eta$) to a rotational viscosity just after preparation ($\eta_0$).

| | Just after preparation | After 1 day | After 5 days | After 14 days |
|---|---|---|---|---|
| Comparative Example 1 | 1 | 0.55 | 0.46 | 0.42 |
| Comparative Example 2 | 1 | 0.84 | 0.78 | 0.69 |
| Comparative Example 3 | 1 | 0.69 | 0.64 | 0.57 |
| Example 1 | 1 | 0.93 | 0.98 | 0.94 |
| Example 2 | 1 | 0.80 | 0.77 | 0.76 |
| Example 3 | 1 | 0.93 | 0.93 | 0.94 |

As can be seen from the data shown in the above table, the emulsions prepared in Examples 1, 2 and 3 using the present combinations of branched polysiloxanes and polyether-modified branched polysiloxanes caused small changes in viscosity with the passage of time, compared with emulsions prepared in Comparative Examples 1,2 and 3. In other words, it was demonstrated that stable emulsions were prepared in accordance with the invention.

EXAMPLE 4

Lipstick containing the following ingredients was prepared in accordance with the process described below:

| Ingredients | Amount mixed (%) |
|---|---|
| 1. Dextrin palmitate ethylhexanoate | 9.0 |
| 2. Glyceryl triisooctanoate | 22.0 |
| 3. Bentonite | 0.7 |
| 4. Siloxane compound of Synthesis Example 14 | 1.5 |
| 6. Siloxane compound of Synthesis Example 1 | 42.0 |
| 7. 1,3-Butylene glycol | 5.0 |
| 8. Colored pigment | proper |

[Preparation Process]

A: The ingredient 1, a part of the ingredient 2, and the ingredients 3 to 5 were mixed together, and made into a solution.

B: The ingredient 8 was mixed with the remainder of the ingredient 2, and dispersed therein with a roller.

C: The dispersion prepared in the step B was added to the solution prepared in the step A, and mixed homogeneously.

D: The ingredients 6 and 7 were mixed together, and warmed.

E: The mixture prepared in the step D was added to the homogenous mixture obtained in the step C, and subjected to emulsification.

It has been shown that the thus prepared lipstick was creamy lipstick having excellent makeup durability, spread well and had neither tacky feel nor oily feel.

EXAMPLE 5

Eyeliner containing the following ingredients was prepared in accordance with the process described below:

| Ingredients | Amount mixed (%) |
|---|---|
| 1. Siloxane compound of Synthesis Example 1 | rest |
| 2. Siloxane compound of Synthesis Example 17 | 3.0 |
| 3. Siloxane compound of Synthesis Example 12 | 15.0 |
| 4. Dioctadecyldimethylammonium salt-modified montmorillonite | 3.0 |
| 5. Silicone-treated iron oxide black[*)] | 10.0 |
| 6. 1,3-Butylene glycol | 5.0 |
| 7. Antiseptic | proper |
| 8. Perfume | proper |
| 9. Purified water | 10.0 |

[*)]: The silicone-treated iron oxide black was prepared by adding methylhydrogenpolysiloxane in a proportion of 2% to the iron oxide black and heating them.

[Preparation Process]

A: The ingredients 1 to 4 were mixed together, and thereto the ingredient 5 was further added. These ingredients were dispersed homogeneously.

B: The ingredients 6 to 8 were mixed.

C: The mixture obtained in the step B was added little by little to the dispersion obtained in the step A to make an emulsion, and then the ingredient 9 was added to the emulsion.

The thus prepared eyeliner spread smoothly, and so the users thereof were able to outline the eyes easily. Further, this eyeliner had no tacky feel, but provided cool and dry feelings to the users. In addition, it was proved that the present eyeliner caused no change in quality by temperature and aging and the duration of its effect was very long because of its high resistance to water and sweat. In other words, the eyeliner obtained had very excellent usability and stability,

EXAMPLE 6

Eye shadow constituted of the following ingredients was prepared in accordance with the process described below:

| Ingredients | Amount mixed (%) |
|---|---|
| 1. Siloxane compound of Synthesis Example 1 | 15.0 |
| 2. Siloxane compound of Synthesis Example 9 | 10.0 |
| 3. Siloxane compound of Synthesis Example 14 | 2.0 |
| 4. PEG (10) lauryl ether | 0.5 |
| 5. Silicone-treated chromium oxide[*1)] | 6.2 |
| 6. Silicone-treated ultramarine blue[*1)] | 4.0 |

-continued

| Ingredients | Amount mixed (%) |
|---|---|
| 7. Titanium-coated mica treated with Silicone*[1] | 6.0 |
| 8. Sodium chloride | 2.0 |
| 9. Propylene glycol | 8.0 |
| 10. Antiseptic | proper |
| 11. Perfume | proper |
| 12. Purified water | the rest |

*[1]: Silicone-treated powder was prepared by adding methylhydrogenpolysiloxane in a proportion of 3% to powder and heating them.

[Preparation Process]

A: The ingredients 1 to 4 were mixed together, and thereto the ingredients 5 to 7 were further added. These ingredients were dispersed homogeneously.

B: The ingredients 8, 9, 10 and 12 were mixed to make a homogeneous solution.

C: The solution obtained in the step B was added little by little to the dispersion obtained in the step A with stirring, thereby making an emulsion, and then the ingredient 11 was added to the emulsion.

The thus prepared eye shadow spread lightly and smoothly, had neither oily nor powdery feel, and provided moist and refreshing feelings to the users. Further, it was proved that the present eye shadow ensured durable makeup effect to the users because of its high water-resistance, water repellency and sweat resistance, and besides, caused no change by fluctuation of temperature and passage of time, namely it had very high stability.

Example 7

Suntan milk constituted of the following ingredients was prepared in accordance with the process described below:

| Ingredients | Amount mixed (wt %) |
|---|---|
| 1. Emulsifier composition (*1) | 6.0 |
| 2. Siloxane compound of Synthesis Example 2 | 49.0 |
| 3. 1,3-Butylene glycol | 5.0 |
| 4. Sodium dehydroacetate | proper |
| 5. Antioxidant | proper |
| 6. Antiseptic | proper |
| 7. Perfume | proper |
| 8. Purified water | the rest |

(*1) Emulsifier composition constituted of:
a. 10.0 parts by weight of a silicone compound synthesized in Synthesis Example 14
b. 10.0 parts by weight of dioctadecyldimethylammonium salt-modified montmorillonite,
c. 40.0 parts by weight of ethanol.

[Preparation Process]

A: The ingredient a was dissolved in the ingredient c, and thereto the ingredient b was added.

B: The admixture obtained in the step A was stirred for 1 hour with a dispersion mill, and then the ethanol was removed therefrom with an evaporator.

C: The residue obtained in the step B was dried at 50° C. for twenty-four hours to prepare an emulsifier composition as the ingredient 1.

D: The ingredient 1 was mixed with the ingredient 2.

E: The ingredients 3 to 6 and 8 were mixed homogeneously.

F: To the mixture obtained in the step D with stirring, the homogeneous mixture obtained in the step E was added little by little to make an emulsion, and then the ingredient 7 was added to the emulsion.

The thus prepared suntan milk had a fine texture, spread smoothly and lightly, had neither tacky nor oily feel, and gave moist and fresh feel to the users' skin. Further, this milk had high resistance to water and the effect thereof kept for a long time. In addition, it was proved that the present suntan milk caused no change in quality by temperature changes and elapsed time, namely, it had very excellent stability.

EXAMPLE 8

Sun cut cream constituted of the following ingredients was prepared in accordance with the process described below:

| Ingredients | Amount mixed (wt %) |
|---|---|
| 1. Decamethylcyclopentasiloxane | 17.5 |
| 2. KP545 (*1) | 12.0 |
| 3. Glyceryl triisooctanoate | 5.0 |
| 4. Octyl paramethoxycinnamate | 6.0 |
| 5. KSG21 (*2) | 5.0 |
| 6. Siloxane compound of Synthesis Example 15 | 1.0 |
| 7. Zinc oxide treated so as to have affinity for oil | 20.0 |
| 8. Sodium chloride | 0.5 |
| 9. 1,3-Butylene glycol | 2.0 |
| 10. Antiseptic | proper |
| 11. Perfume | proper |
| 12. Purified water | the rest |

(*1) Decamethylcyclopentasiloxane solution of acryl-silicone resin produced by Shin-Etsu Chemical Co., Ltd.
(*2) Dimethylpolysiloxane (6 mm$^2$/s) solution of cross-linked silicone resin produced by Shin-Etsu Chemical Co., Ltd.

[Preparation Process]

A: The ingredient 2 was added to a part of the ingredient 1, and these ingredients were homogenized. Therein, the ingredient 7 was admixed, and dispersed by means of a beads mill.

B: The rest of the ingredient 1 and the ingredients 3 to 6 were mixed together to make a homogeneous mixture.

C: The ingredients 8 to 10 and 12 were mixed and dissolved.

D: The mixture obtained in the step B was added to the solution obtained in the step C, followed by emulsifying treatment. To the emulsion obtained, the dispersion obtained in the step A and the ingredient 11 were further added.

The thus prepared sun cut cream had no tacky feel, not only spread smoothly but also provided clingy feeling and fitted in with the skin, and further ensured lustrous finish and durable makeup effects. In addition, it was proved that the present cream caused no change in quality by of temperature changes and lapsed time, namely it had very high stability.

EXAMPLE 9

Suntan cream constituted of the following ingredients was prepared in accordance with the process described below:

| Ingredients | Amount mixed (wt %) |
|---|---|
| 1. Siloxane compound of Synthesis Example 1 | 15.0 |
| 2. Siloxane compound of Synthesis Example 8 | 5.0 |
| 3. Silicone wax | 0.5 |
| 4. Siloxane compound of Synthesis Example 14 | 6.0 |
| 5. Palmitic acid | 0.2 |
| 6. Dimethyloctylparaaminobenzoic acid | 0.5 |
| 7. 4-t-Butyl-4'-methoxy-dibenzoylmethane | 0.5 |
| 8. Kaolin | 0.5 |
| 9. Iron oxide red | 0.2 |
| 10. Iron oxide yellow | 0.3 |

-continued

| Ingredients | Amount mixed (wt %) |
|---|---|
| 11. Iron oxide black | 0.1 |
| 12. Titanium dioxide-coated mica | 1.0 |
| 13. Sodium L-glutamate | 3.0 |
| 14. 1,3-Butylene glycol | 5.0 |
| 15. Dioctadecyldimethylammonium chloride | 0.1 |
| 16. Antioxidant | proper |
| 17. Antiseptic | proper |
| 18. Perfume | proper |
| 19. Purified water | the rest |

[Preparation Process]

A: The ingredients 1 to 7, 16 and 17 were mixed and heated to prepare a solution.
B: The ingredient 15 and a part of the ingredient 19 were mixed and heated with stirring, and thereto the ingredients 8 to 12 were added, followed by dispersion treatment.
C: The ingredients 13 and 14 and the rest of the ingredient 19 were made into a homogeneous solution, and mixed with the dispersion obtained in the step B.
D: To the solution prepared in the step A with stirring, the mixture obtained in the step C was added little by little to prepare an emulsion. The emulsion prepared was cooled, and thereto the ingredient 18 was added.

The thus prepared suntan cream had a fine texture, spread smoothly and lightly, had neither tacky nor oily feel, and gave moist and fresh feel to the users' skin. Further, this cream gave a feeling of good fit to the users and the effect thereof kept for a long time. In addition, it was proved that the present suntan cream caused neither separation of ingredients nor flocculation of powders by change in temperature and storage, namely, it had very excellent stability.

EXAMPLE 10

Foundation constituted of the following ingredients was prepared in accordance with the process described below:

| Ingredients | Amount mixed (wt %) |
|---|---|
| 1. Siloxane compound of Synthesis Example 1 | 45.0 |
| 2. Dimethylpolysiloxane (6 mm²/s) | 5.0 |
| 3. Siloxane compound of Synthesis Example 14 | 1.5 |
| 4. Siloxane compound of Synthesis Example 15 | 0.5 |
| 5. Octadecyldimethylbenzylammonium salt-modified montmorillonite | 4.0 |
| 6. Titanium dioxide treated so as to have hydrophobicity (*1) | 10.0 |
| 7. Talc treated so as to have hydrophobicity (*1) | 6.0 |
| 8. Mica treated so as to have hydrophobicity (*1) | 6.0 |
| 9. Ion oxide red treated so as to have hydrophobicity (*1) | 1.6 |
| 10. Iron oxide yellow treated so as to have hydrophobicity (*1) | 0.7 |
| 11. Iron oxide black treated so as to have hydrophobicity (*1) | 0.2 |
| 12. Dipropylene glycol | 5.0 |
| 13. Methyl paraoxybenzoate | 0.3 |
| 14. 2-Amino-2-methyl-1,3-propanediol | 0.2 |
| 15. Hydrochloric acid | 0.1 |
| 16. Perfume | proper |
| 17. Purified water | the rest |

(*1) Each powder was rendered hydrophobic by treatment with methylhydrogenpolysiloxne added thereto in a proportion of 2 wt % and subsequent heating.

[Preparation Process]

A: The ingredients 1 to 5 were mixed together under heating, and thereto the ingredients 6 to 11 were added. Then, the resulting admixture was homogenized.
B: The ingredients 12 to 15 and 17 were mixed together, and made into a solution by heating (the pH of the aqueous phase was 9.0).
C: The solution obtained in the step B was added little by little to the homogeneous dispersion obtained in the step A with stirring, thereby making an emulsion. After the emulsion was cooled, the ingredient 16 was added thereto.

The foundation thus prepared had fine texture, spread lightly and smoothly, had neither oily nor tacky feel, and rendered the skin moist, youthful and refreshing. Further, it was proved that this foundation ensured durable makeup effect, and besides, caused no change by temperature changes and elapsed time, namely it had very high stability.

EXAMPLE 11

Liquid foundation constituted of the following ingredients was prepared in accordance with the process described below:

| Ingredients | Amount mixed (wt %) |
|---|---|
| 1. Siloxane compound of Synthesis Example 1 | 16.0 |
| 2. Siloxane compound of Synthesis Example 9 | 8.0 |
| 3. Octyl paramethoxycinnamate | 3.0 |
| 4. 12-Hydroxystearic acid | 1.0 |
| 5. Siloxane compound of Synthesis Example 5 | 15.0 |
| 6. Siloxane compound of Synthesis Example 16 | 5.0 |
| 7. Spherical silicone resin powder (*1) | 3.0 |
| 8. Fluorine compound-treated fine-grain titanium dioxide (*2) | 8.0 |
| 9. Fluorine compound-treated titanium mica (*2) | 1.0 |
| 10. Fluorine compound-treated titanium dioxide (*2) | 5.0 |
| 11. Fluorine compound-treated iron oxide red (*2) | 0.9 |
| 12. Fluorine compound-treated iron oxide yellow (*2) | 2.0 |
| 13. Fluorine compound-treated iron oxide black (*2) | 1.0 |
| 14. Ethanol | 15.0 |
| 15. Glycerin | 3.0 |
| 16. Magnesium sulfate | 1.0 |
| 17. Antiseptic | proper |
| 18. Perfume | proper |
| 19. Purified water | the rest |

(*1) KMP590 (trade name, produced by Shin-Etsu Chemical Co., Ltd.)
(*2) Each powder was treated with diethanolamine salt of perfluoroalkylethylphosphoric acid added in a proportion of 5% to the powder.

[Preparation Process]

A: The ingredients 7 to 13 were mixed homogeneously.
B: The ingredients 1 to 6 were mixed under heating at 70° C., and thereto the mixture obtained in the step A was added to make a homogeneous dispersion.
C: The ingredients 14 to 17 and 19 were warmed to 40° C., and then added to the dispersion obtained in the step B and made into an emulsion. After cooling, the emulsion was admixed with the ingredients 18.

The thus prepared liquid foundation had no tackiness, spread smoothly, and gave a strong feeling of refreshment to the users. Further, it was proved that this foundation caused no change in quality by temperature changes and elapsed time, namely it had very high stability.

EXAMPLE 12

Hair cream constituted of the following ingredients was prepared in accordance with the process described below:

| Ingredients | Amount mixed (wt %) |
| --- | --- |
| 1. Siloxane compound of Synthesis Example 9 | 10.0 |
| 2. Siloxane compound of Synthesis Example 4 | 5.0 |
| 3. Squalane | 4.0 |
| 4. Siloxane compound of Synthesis Example 12 | 1.0 |
| 5. Glyceryl dioleate | 2.0 |
| 6. Siloxane compound of Synthesis Example 15 | 4.0 |
| 7. Sodium sorbitol sulfate | 2.0 |
| 8. Sodium chondroitin sulfate | 1.0 |
| 9. Sodium hyaluronate | 0.5 |
| 10. Propylene glycol | 3.0 |
| 11. Antiseptic | 1.5 |
| 12. Vitamin E acetate | 0.1 |
| 13. Antioxidant | proper |
| 14. Perfume | proper |
| 15. Purified water | the rest |

[Preparation Process]

A: The ingredients 1 to 6, 11 and 12 were mixed under heating.

B: The ingredients 7 to 10 and 15 were mixed and dissolved under heating.

C: To the mixture obtained in the step A with stirring, the mixture obtained in the step B was added little by little to make an emulsion. The emulsion was cooled, and then admixed with the ingredient 14.

The thus prepared hair cream spread smoothly, had neither tacky nor oily feel, and gave a moist, fresh and refreshing feel to the users' hair. Further, it was proved that this hair cream kept its effect for a long time because of its good water resistance, water repellency and perspiration resistance, and besides, caused no change by temperature changes and elapsed time, namely it had very high stability.

EXAMPLE 13

Hair cream constituted of the following ingredients was prepared in accordance with the process described below:

| Ingredients | Amount mixed (wt %) |
| --- | --- |
| 1. Siloxane compound of Synthesis Example 11 | 18 |
| 2. Siloxane compound of Synthesis Example 12 | 6 |
| 3. Glyceryl tri-2-ethylhexanoate | 8 |
| 4. Vaseline | 5 |
| 5. Stearyl alcohol | 2 |
| 6. Sorbitan monooleate | 2 |
| 7. Siloxane compound of Synthesis Example 17 | 2 |
| 8. Glycerol | 5 |
| 9. Perfume | proper |
| 10. Purified water | the rest |

[Preparation Process]

A: The ingredients 1 to 7 were mixed and dissolved at 70° C.

B: The ingredients 8 to 10 were mixed with stirring, and thereto the solution prepared in the step A was added and made into an emulsion.

It was proved that the thus prepared hair cream imparted a good shine and smoothness to hair and had excellent hair setting effect.

EXAMPLE 14

Moisture-retentive cream constituted of the following ingredients was prepared in accordance with the process described below:

| Ingredients | Amount mixed (wt %) |
| --- | --- |
| 1. Siloxane compound of Synthesis Example 9 | 10.0 |
| 2. Siloxane compound of Synthesis Example 4 | 3.0 |
| 3. Liquid paraffin | 5.0 |
| 4. Siloxane compound of Synthesis Example 3 | 8.0 |
| 5. Silicone compound of Synthesis Example 18 | 2.0 |
| 6. Spherical powder of organopolysiloxane elastomer (*1) | 2.5 |
| 7. Hydrophobic silica (*2) | 2.0 |
| 8. Zinc stearate | 2.0 |
| 9. Vitamin E acetate | 3.0 |
| 10. Polyethylene glycol 400 | 1.0 |
| 11. Sodium lactate | 1.0 |
| 12. 1,3-Butylene glycol | 5.0 |
| 13. Antiseptic | proper |
| 14. Perfume | proper |
| 15. Purified water | the rest |

(*1) KMP594 (trade name, produced by Shin-Etsu Chemical Co., Ltd.)
(*2) Aerosil R972 (trade name, produced by Nippon Aerosil Co., Ltd.)

[Preparation Process]

A: The ingredients 1 to 5, 8 and 9 were mixed homogeneously, and thereto the ingredients 6 and 7 were added and made into a homogeneous dispersion.

B: The ingredients 10 to 13 and 15 were added, and made into a solution.

C: The solution obtained in the step B was added little by little to the dispersion obtained in the step A to make an emulsion. The emulsion prepared was cooled, and thereto the ingredient 14 was added.

The thus prepared moisture-retentive cream spread lightly and smoothly, and had a moist and fresh feel, but no tacky feel. Further, it was proved that this cream had excellent usability and stability, and caused no change in quality by temperature changes and elapsed time.

EXAMPLE 15

Hand cream constituted of the following ingredients was prepared in accordance with the process described below:

| Ingredients | Amount mixed (wt %) |
| --- | --- |
| 1. Siloxane compound of Synthesis Example 1 | 30.0 |
| 2. Liquid paraffin | 10.0 |
| 3. Siloxane compound of Synthesis Example 13 | 15.0 |
| 4. Siloxane compound of Synthesis Example 14 | 4.0 |
| 5. Distearyldimethylammonium chloride | 0.8 |
| 6. Vitamin E acetate | 0.1 |
| 7. Polyethylene glycol 4000 | 1.0 |
| 8. Glycerin | 10.0 |
| 9. Aluminum magnesium silicate | 1.2 |
| 10. Antiseptic | proper |
| 11. Perfume | proper |
| 12. Purified water | the rest |

[Preparation Process]

A: The ingredients 1 and 3 were mixed and dissolved under heating, and thereto the ingredients 2, 4 to 6 and 10 were added under heating.

B: The ingredients 7 to 9 and 12 were mixed and dissolved under heating.

C: To the mixture obtained in the step A, the solution obtained in the step B was added little by little to make an emulsion. The emulsion was cooled, and then admixed with the ingredient 11.

The thus prepared hand cream spread smoothly, had no tacky feel, and gave a refreshing feel to the users' hand.

Further, it was proved that this cream effectively protected hand skin from getting rough from washing work, and besides, it was highly stable to temperature changes.

EXAMPLE 16

Oil-in-water (O/W) hand cream constituted of the following ingredients was prepared in accordance with the process described below:

| Ingredients | Amount mixed (wt %) |
| --- | --- |
| 1. KP545 (*1) | 10.0 |
| 2. KP561 (*2) | 8.0 |
| 3. Cetanol | 1.0 |
| 4. Glyceryl triisostearate | 5.0 |
| 5. Stearic acid | 3.0 |
| 6. Glyceryl monostearate | 1.5 |
| 7. Siloxane compound of Synthesis Example 15 | 0.7 |
| 8. Sorbitan sesqui-oleate | 0.5 |
| 9. Polyoxyethylenesorbitan monooleate | 1.0 |
| 10. Sodium hydroxide (1% aq. soln.) | 10.0 |
| 11. 1,3-Butylene glycol | 5.0 |
| 12. Antiseptic | proper |
| 13. Perfume | proper |
| 14. Purified water | the rest |

(*1) Decamethylcyclopentasiloxane solution of acrylsilicone resin produced by Shin-Etsu Chemical Co., Ltd.
(*2) Stearyl-modified acrylsilicone resin produced by Shin-Etsu Chemical Co., Ltd.

[Preparation Process]
A: The ingredients 1 to 9 were mixed, and made into a solution under heating.
B: The ingredients 10 to 12 and 14 were mixed and heated.
C: The mixture obtained in the step B was added to the solution obtained in the step A, and made into an emulsion. After cooling the emulsion, the ingredient 13 was further added thereto.

The thus prepared O/W hand cream had no tacky feel, not only spread smoothly but also provided a clingy feeling and fitted in with the skin, and further ensured shiny finish and durable effect. In addition, it was proved that this cream was very stable to temperature changes and lapsed time.

EXAMPLE 17

Milky lotion constituted of the following ingredients was prepared in accordance with the process described below:

| Ingredients | Amount mixed (wt %) |
| --- | --- |
| 1. Siloxane compound of Synthesis Example 9 | 15.0 |
| 2. Siloxane compound of Synthesis Example 4 | 5.0 |
| 3. Squalane | 5.0 |
| 4. Pentaerythritol tetra-2-ethylhexanoate | 5.0 |
| 5. Siloxane compound of Synthesis Example 15 | 3.0 |
| 6. Spherical powder of organopolysiloxane elastomer (*1) | 2.0 |
| 7. Hydrophobic silica (*2) | 0.5 |
| 8. Magnesium salt of phosphoascorbate | 1.0 |
| 9. Sodium chloride | 1.0 |
| 10. Polyethylene glycol 11000 | 1.0 |
| 11. Propylene glycol | 8.0 |
| 12. Antiseptic | proper |
| 13. Perfume | proper |
| 14. Purified water | the rest |

(*1) KMP594 (trade name, produced by Shin-Etsu Chemical Co., Ltd.)
(*2) Aerosil R972 (trade name, produced by Nippon Aerosil Co., Ltd.)

[Preparation Process]
A: The ingredients 1 to 5 were mixed homogeneously, and thereto the ingredients 6 and 7 were added and made into a homogeneous dispersion.
B: The ingredients 8 to 10 were added to the ingredient 14, and dissolved therein, and thereto a homogeneous mixture of the ingredients 11 and 12 were added.
C: The admixture obtained in the step B was added little by little to the dispersion obtained in the step A to make an emulsion. The emulsion prepared was cooled, and thereto the ingredient 13 was added.

The thus prepared milky lotion spread lightly, and had no tacky feel but dry and smooth feel. Further, it was proved that this lotion had excellent usability and stability, and caused no change in quality by temperature changes and elapsed time.

EXAMPLE 18

Beauty-care lotion (or moisturizing essence) constituted of the following ingredients was prepared in accordance with the process described below:

| Ingredients | Amount mixed (wt %) |
| --- | --- |
| 1. Siloxane compound of Synthesis Example 1 | 12.0 |
| 2. Glyceryl triisooctanoate | 10.0 |
| 3. Siloxane compound of Synthesis Example 15 | 2.0 |
| 4. Siloxane compound of Synthesis Example 14 | 0.2 |
| 5. Glycerin | 10.0 |
| 6. Magnesium salt of phospho ascorbate | 3.0 |
| 7. Sodium chloride | 2.0 |
| 8. Antiseptic | proper |
| 9. Perfume | proper |
| 10. Purified water | the rest |

[Preparation Process]
A: The ingredients 1 to 4 were mixed together under heating.
B: The ingredients 5 to 8 and 10 were heated and dissolved homogeneously.
C: The solution obtained in the step B was added little by little to the mixture obtained in the step A with stirring, and made into an emulsion. After the emulsion was cooled, the ingredient 9 was added thereto.

The beauty-care lotion thus prepared had fine texture, spread smoothly, and had no tackiness. And it gave moist and youthful feelings to the users. Further, it was proved that this lotion caused no change in quality by temperature changes and elapsed time, namely it had very high stability.

EXAMPLE 19

Antiperspirant constituted of the following ingredients was prepared in accordance with the process described below:

| Ingredients | Amount mixed (wt %) |
| --- | --- |
| 1. Siloxane compound of Synthesis Example 1 | 30.0 |
| 2. Siloxane compound of Synthesis Example 14 | 1.0 |
| 3. Polyoxyethylenesorbitan monooleate (number of oxyethylene units: 20) | 0.5 |
| 4. Glycine salt of aluminum zirconium tetrachlorohydrate | 20.0 |
| 5. Purified water | the rest |

[Preparation Process]
A: The ingredients 1 and 2 were mixed together.
B: The ingredient 4 was dissolved in the ingredient 5, and thereto the ingredient 3 was added.
C: The solution obtained in the step B was added little by little to the mixture obtained in the step A with stirring to make an emulsion.

The thus prepared antiperspirant spread smoothly, had neither tacky nor oily feel, little developed a powdery bloom on the applied skin, and gave a refreshing feeling to the users. Further, it was proved that this antiperspirant caused no change in quality by temperature changes and elapsed time, namely it had high stability.

EXAMPLE 20

Cleansing cream constituted of the following ingredients was prepared in accordance with the process described below:

| Ingredients | Amount mixed (wt %) |
| --- | --- |
| 1. Siloxane compound of Synthesis Example 9 | 5.0 |
| 2. Siloxane compound of Synthesis Example 4 | 5.0 |
| 3. Liquid paraffin | 8.0 |
| 4. Jojoba oil | 2.0 |
| 5. Siloxane compound of Synthesis Example 14 | 2.5 |
| 6. Siloxane compound of Synthesis Example 15 | 0.5 |
| 7. Dextrin fatty acid ester | 0.8 |
| 8. Aluminum monostearate | 0.2 |
| 9. Aluminum chloride | 1.0 |
| 10. Glycerin | 10.0 |
| 11. Antiseptic | proper |
| 12. Perfume | proper |
| 13. Purified water | the rest |

[Preparation Process]
A: The ingredients 1 to 8 were mixed under heating.
B: The ingredients 9, 10, 11 and 13 were mixed and dissolved under heating.
C: The solution obtained in the step B was added little by little to the mixture obtained in the step A with stirring to make an emulsion. After cooling, the emulsion was admixed with the ingredient 12.

The thus prepared cleansing cream had fine texture, spread smoothly, had neither tacky nor oily feel, gave moist, youthful and refreshed feelings to the users, and had high cleansing effect. Further, it was proved that this cleansing cream caused no change in quality by temperature changes and elapsed time, namely it had high stability.

EXAMPLE 21

Treatment gel constituted of the following ingredients was prepared in accordance with the process described below:

| Ingredients | Amount mixed (wt %) |
| --- | --- |
| 1. Ethanol | 20.0 |
| 2. Siloxane Compound of Synthesis Example 17 | 0.5 |
| 3. Glyceryl triisooctanoate | 3.0 |
| 4. Siloxane Compound of Synthesis Example 7 | 2.0 |
| 5. KSP-100 (*1) | 8.0 |
| 6. Carobxyvinyl powder (1% aq. soln.) | 20.0 |
| 7. Triethanolamine | 0.2 |
| 8. Purified water | 46.3 |

(*1) Vinyldimethicone/methicone silsesquioxane cross-polymer produced by Shin-Etsu Chemical Co., Ltd.

[Preparation Process]
A: The ingredients 1 to 5 were mixed and dispersed.
B: The ingredients 6 to 8 were mixed and homogenized.
C: The homogeneous mixture obtained in the step B was added little by little to the dispersion obtained in the step A and homogeneously mixed together.

The thus prepared treatment gel spread lightly, had neither tacky nor oily feel, gave moist, youthful and refreshing feelings to users thereof, and fitted in with the skin. In addition, it was proved that this treatment gel caused no change in quality by of temperature changes and lapsed time, namely it had excellent stability.

EXAMPLE 22

Wash-away type facial pack constituted of the following ingredients was prepared in accordance with the process described below:

| Ingredients | Amount mixed (wt %) |
| --- | --- |
| 1. Siloxane compound of Synthesis Example 9 | 3.0 |
| 2. Siloxane compound of Synthesis Example 14 | 2.0 |
| 3. Kaolin | 30.0 |
| 4. Carboxyvinyl polymer | 0.4 |
| 5. 1,3-Butylene glycol | 10.0 |
| 6. Glycerin | 20.0 |
| 7. Antiseptic | proper |
| 8. Perfume | proper |
| 9. Purified water | the rest |

[Preparation Process]
A: The ingredients 1, 2 and 8 were mixed together.
B: The ingredients 4 to 7 and 9 were mixed homogeneously, and further admixed with the ingredient 3 with stirring.
C: The mixture obtained in the step A was added to the mixture obtained in the step B and emulsified. Thus, a wash-away type facial pack in a paste state was prepared.

The thus prepared facial pack spread smoothly, and had excellent cleansing effect. In addition, it gave pleasant feelings to users thereof. Specifically, after the facial pack was washed away, the face had moist, soft and smooth feel but no tackiness. Further, it was proved that the facial pack had excellent stability.

EXAMPLE 23

Deodorant constituted of the following ingredients was prepared in accordance with the process described below:

| Ingredients | Amount mixed (wt %) |
| --- | --- |
| 1. Siloxane compound of Synthesis Example 1 | 12.0 |
| 2. Siloxane compound of Synthesis Example 9 | 4.0 |
| 3. Siloxane compound of Synthesis Example 14 | 1.0 |
| 4. Propylene glycol | 31.0 |
| 5. Triclosan | 0.1 |
| 6. Glycerin | 15.0 |
| 7. Antiseptic | proper |
| 8. Perfume | proper |
| 9. Purified water | the rest |

[Preparation Process]
A: The ingredients 1 to 3 were mixed.
B: The ingredient 5 was dissolved in the ingredient 4, and further admixed with the ingredients 6 to 9.
C: The mixture obtained in the step A was stirred vigorously, and thereto the mixture obtained in the step B was added to make an emulsion.
D: The emulsion obtained in the step C in an amount of 65 parts by weight and a jetting agent (mixture of n-butane, isobutane and propane) in an amount of 35 parts by weight were charged into aerosol cans.

The thus prepared deodorant had excellent usability, because it didn't trickled down even when used in a high concentration, but it had no tacky feel but a dry and smooth feel. Further, the duration of its effect was long.

Advantages of the Invention

The present cosmetics in which the present siloxane compounds are incorporated spread smoothly, have no oily feel, and render the skin moist, fresh and youthful. Further, they provide a refreshed feel and durable makeup effect to users thereof, and besides, cause no change by fluctuation of temperature and passage of time, namely have very high stability.

Besides having the foregoing characteristics, such as use comfort, excellent usability and high stability to aging the skin cleansing compositions in which the present siloxane compounds are mixed can acquire a characteristic that they absorb cosmetics and sebum stains very well and remove them efficiently.

What is claimed is:

1. A cosmetic material comprising: as essential cosmetic constituents, (A) a silicone-branched silicone compound of the formula (1):

wherein each $R^1$ is independently a hydrogen atom or an organic group selected from 1–30C alkyl groups, aryl groups, aralkyl aroups, fluorinated alkyl groups or organic groups of the formula (2),

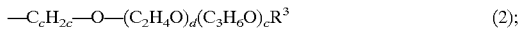

each $R^2$ is independently a silicone compound residue of the formula (3),

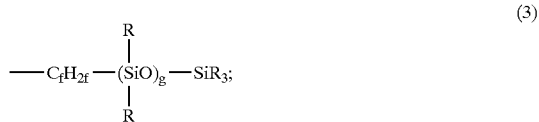

a is a number satisfying inequality $1.0 \leq a \leq 2.5$; b is a number satisfying inequality $0.001 \leq b \leq 1.5$; c is an integer satisfying inequality $0 \leq c \leq 15$; d is an integer satisfying inequality $0 \leq d \leq 50$; e is an integer satisfying inequality $0 \leq e \leq 50$; f is an integer satisfying inequality $1 \leq f \leq 5$; g is an integer satisfying inequality $0 \leq g \leq 500$; each R is independently a 1–30C alkyl group, an aryl group, an aralkyl group or a fluorinated alkyl group; $R^3$ is a 4–30C monovalent hydrocarbon group, or an organic group $R^4$—(CO)— where $R^4$ is a 1–30C monovalent hydrocarbon group; and (B) a silicone-branched polyether-modified silicone compound of the formula (9):

wherein each $R^8$ is independently an organic group selected from 1–30C alkyl groups, aryl groups, aralkyl groups, fluorinated alkyl groups, amino-substituted alkyl group, carboxyl-substituted alkyl groups or organic groups of the formula (10),

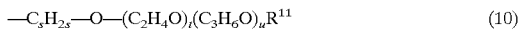

each $R^9$ is independently an polyoxyalkylene group of the formula (11),

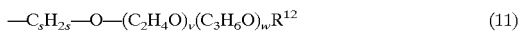

each $R^{10}$ is independently an organosiloxane residue of the formula (12),

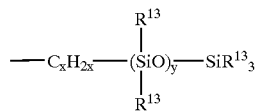

$R^{11}$ is a 10–30C monovalent hydrocarbon group, or an organic group $R^{14}$—(CO)—; $R^{12}$ is a hydrogen atom, a 1–9C monovalent hydrocarbon group, or an organic group $R^{15}$—(CO)—; $R^{14}$ is a 9–30C monovalent hydrocarbon group; $R^{15}$ is a 1–8C monovalent hydrocarbon group; each $R^{13}$ is independently a 1–30C alkyl group, an aryl group, an aralkyl group or a fluorinated alkyl group; p is a number satisfying inequality $1.0 \leq n \leq 2.5$; q is a number satisfying inequality $0.001 \leq q \leq 1.5$; r is a number satisfying inequality $0.001 \leq r \leq 1.5$; s is an integer satisfying inequality $0 \leq c \leq 15$; t is an integer satisfying inequality $0 \leq t \leq 50$; u is an integer satisfying inequality $0 \leq u \leq 50$; v and w are integers satisfying inequality $2 \leq v \leq 200$ and $2 \leq w \leq 200$, provided that $2 \leq y+w \leq 200$; x is an integer satisfying inequality $1 \leq x \leq 15$; and y is an integer satisfying inequality $0 \leq y \leq 500$.

2. A cosmetic material according to claim 1, wherein the silicone-branched silicone compound (A) is prepared by polymerizing a branched silicone compound containing units of the formula (4) with a cyclic silicone compound of the formula (5), a linear silicone compound of the formula (6) or a mixture of silicone compounds of the formulae (5) and (6) respectively in the presence of an acid or alkali catalyst:

wherein an i/h ratio is from 0.3 to 1.5 and each $R^5$ is independently a hydrogen atom or an organic group selected from 1–30C alkyl groups, aryl groups, aralkyl groups, fluorinated alkyl groups, amino-substituted alkyl groups, carboxyl-substituted alkyl groups or 1–6C alkoxy groups;

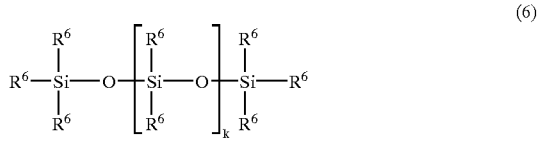

wherein j is an integer of from 3 to 10, k is an integer of from 0 to 100, and each $R^6$ is independently a hydrogen atom or an organic group selected from 1–30C alkyl groups, aryl groups, aralkyl groups, fluorinated alkyl groups, amino-substituted alkyl groups, carboxyl-substituted alkyl groups or 1–6C alkoxy groups.

3. A cosmetic material according to claim 1, wherein the silicone-branched silicone compound (A) is prepared by polymerizing a silicone compound of the formula (7) with a cyclic silicone compound of the formula (5), a linear silicone compound of the structural formula (6) or a mixture of silicone compounds of the formulae (5) and (6) respectively in the presence of an acid or alkali catalyst:

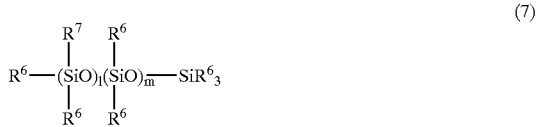
(7)

wherein each $R^6$ is independently a hydrogen atom or an organic group selected from 1–30C alkyl groups, aryl groups, aralkyl groups, fluorinated alkyl groups, amino-substituted alkyl groups, carboxyl-substituted alkyl groups or 1–6C alkoxy groups; each $R^7$ is independently a hydrolyzable group selected from a hydroxyl group or 1–6C alkoxy groups; l is an integer of from 0 to 100; and m is an integer of from 0 to 100.

4. A cosmetic material according to claim 1, wherein the silicone-branched silicone compound (A) is prepared by ring-opening polymerization of a silicone compound of the formula (8) and hexamethylcyclotrisiloxane in the presence of a five-coordinate complex catalyst:

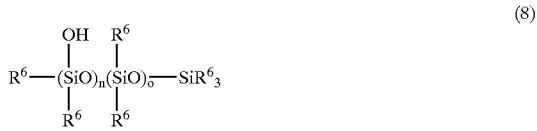
(8)

wherein each $R^6$ is independently a hydrogen atom or an organic group selected from 1–30C alkyl groups, aryl groups, aralkyl groups, fluorinated alkyl groups, amino-substituted alkyl groups, carboxyl-substituted alkyl groups or 1–6C alkoxy groups; n is an integer of from 1 to 500; and o is an integer of from 0 to 500.

5. A cosmetic material according to claim 1, wherein the silicone-branched polyether-modified silicone compound (B) is prepared by addition reaction between a silicone-branched methylhydrogensilicone compound and an organic compound of formula (13), an organic compound of formula (14) or a mixture of these organic compounds, wherein the silicone-branched methylhydrogensilicone compound is prepared by polymerization of a branched silicone compound of formula (4) and a silicone compound of formula (5), a silicone compound of formula (6) or a mixture of compounds represented by formulae (5) and (6) wherein at least one $R^5$ group in formula (4) or at least one $R^6$ group in formula (5) or (6) is a hydrogen atom:

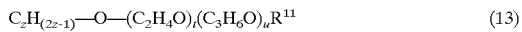
(13)

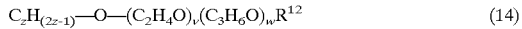
(14)

wherein $R^{11}$ is a 10–30C monovalent hydrocarbon group, or an organic group $R^{14}$—(CO)—; $R^{12}$ is a hydrogen atom, a 1–9C monovalent hydrocarbon group, or an organic group $R^{15}$—(CO)—; $R^{14}$ is a 9–30C monovalent hydrocarbon group; $R^{15}$ is a 1–8C monovalent hydrocarbon group; t is an integer satisfying inequality $0 \leq t \leq 50$; u is an integer satisfying inequality $0 \leq u \leq 50$; v and w are integers satisfying inequality $2 \leq v \leq 200$ and $2 \leq w \leq 200$, provided that $2 \leq v+w \leq 200$; and z is an integer satisfying inequality $3 \leq z \leq 15$.

6. A cosmetic material according to claim 1, wherein the silicone-branched polyether-modified silicone compound (B) is prepared by addition reaction between a silicone-branched methylhydrogensilicone compound and an organic compound of formula (13), an organic compound of formula (14) or a mixture of these organic compounds, wherein the silicone-branched methylhydrogensilicone compound is prepared by polymerization of a silicone compound of formula (7) with a silicone compound of formula (5), a silicone compound of formula (6) or a mixture of compounds of the formulae (5) and (6) wherein at least one group in formulae (5), (6) and (7) is a hydrogen atom:

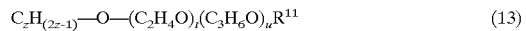
(13)

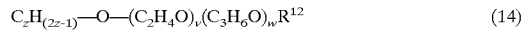
(14)

wherein $R^{11}$ is a 10–30C monovalent hydrocarbon group, or an organic group $R^{14}$—(CO)—; $R^{12}$ is a hydrogen atom, a 1–9C monovalent hydrocarbon group, or an organic group $R^{15}$—(CO)—; $R^{14}$ is a 9–30C monovalent hydrocarbon group; $R^{15}$ is a 1–8C monovalent hydrocarbon group; t is an integer satisfying inequality $0 \leq t \leq 50$; u is an integer satisfying inequality $0 \leq u \leq 50$; v and w are integers satisfying inequality $2 \leq v \leq 200$ and $2 \leq w \leq 200$, provided that $2 \leq v+w \leq 200$; and z is an integer satisfying inequality $3 \leq z \leq 15$.

7. A cosmetic material according to claim 1, wherein the silicone-branched polyether-modified silicone compound (B) is prepared by addition reaction between a silicone-branched methylhydrogensilicone compound and an organic compound of formula (13), an organic compound of formula (14) or a mixture of these organic compounds, wherein the silicone-branched methylhydrogensilicone compound is prepared in the presence of a five-coordinate complex catalyst by ring-opening polymerization of hexamethylcyclotrisiloxane with a silicone compound of the formula (8) wherein at least one $R^6$ group is a hydrogen atom:

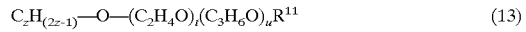
(13)

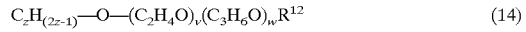
(14)

wherein $R^{11}$ is a 10–30C monovalent hydrocarbon group, or an organic group $R^{14}$—(CO)—; $R^{12}$ is a hydrogen atom, a 1–9C monovalent hydrocarbon group, or an organic group $R^{15}$—(CO)—; $R^{14}$ is a 9–30C monovalent hydrocarbon group; $R^{15}$ is a 1–8C monovalent hydrocarbon group; t is an integer satisfying inequality $0 \leq t \leq 50$; u is an integer satisfying inequality $0 \leq u \leq 50$; v and w are integers satisfying inequality $2 \leq v \leq 200$ and $2 \leq w \leq 200$, provided that $2 \leq v+w \leq 200$; and z is an integer satisfying inequality $3 \leq z \leq 15$.

8. A cosmetic material according to claim 1, further comprising unctuous agents in a proportion of at most 50 weight %.

9. A cosmetic material according to claim 8, wherein at least one of the unctuous agent is an oil.

10. A cosmetic material according to claim 10, wherein at least one of the unctuous agent is a silicone oil containing volatile silicones, a silicone oil having units represented by —[O—Si]$_n$— in its molecular skeleton, or a mixture thereof.

11. A cosmetic material according to claim 8, wherein at least one of the unctuous agent is an oil having fluorine-containing or amino groups.

12. A cosmetic material according to claim 1, further comprising a compound having a hydroxyl group in its molecular structure in a proportion of at most 50.0 weight %.

13. A cosmetic material according to claim 12, wherein the compound having a hydroxyl group in its molecular structure is a monohydric water-soluble alcohol, a polyhydric water-soluble alcohol or a mixture thereof.

14. A cosmetic material according to claim 12, wherein the compound having a hydroxyl group in its molecular structure is a water-soluble polymer.

15. A cosmetic material according to claim 1, further comprising water in a proportion of at most 99.0 weight %.

16. A cosmetic material according to claim 1, further comprising a powder, a coloring material or a mixture thereof.

17. A cosmetic material according to claim 16, wherein at least a part of the powder or the mixture of powder and coloring material is a silicone resin powder, a powder having a silicone elastomer as its skeleton, an organic powder containing units represented by —[O—Si]$_n$—, or a mixture thereof.

18. A cosmetic material according to claim 1, further comprising a surfactant.

19. A cosmetic material according to claim 18, wherein the surfactant is a modified silicone having a polyoxyalkylene chain in its molecule.

20. A cosmetic material according to claim 19, wherein the modified silicone is a compound having an HLB of 2 to 8.

21. A cosmetic material according to claim 1, further comprising cross-linked organopolysiloxanes.

22. A cosmetic material according to claim 21, wherein the cross-linked organopolysiloxanes are cross-linked organopolysiloxanes which cause swelling when they contain a silicone having low viscosity of from 0.65 to 10.0 mm$^2$/s at 25° C. in a quantity larger than the weight of the cross-linked organopolysiloxanes themselves.

23. A cosmetic material according to claim 21, wherein the cross-linked organopolysiloxanes are organopolysiloxanes having a cross-linked structure formed by reaction between hydrogen atoms bonded directly to silicon atoms and a cross-linking agent having at least two vinylic reactive moieties per molecule.

24. A cosmetic material according to claim 21, wherein the cross-linked organopolysiloxanes are organopolysiloxanes having in their cross-links at least one kind of moiety selected from polyoxyalkylene, alkyl, alkenyl, aryl or fluoroalkyl moieties.

25. A cosmetic material according to claim 1, further comprising silicone resin.

26. A cosmetic material according to claim 25, wherein the silicone resin is an acrylsilicone resin.

27. A cosmetic material according to claim 26, wherein the acrylsilicone resin is an acrylsilicone resin containing at least one moiety selected from pyrrolidone, alkyl, polyoxyalkylene or fluoroalkyl moieties.

28. A cosmetic material according to claim 25, wherein the silicone resin is a reticular silicone compound.

29. A cosmetic material according to claim 28, wherein the reticular silicone compound is a reticular silicone compound containing at least one moiety selected from pyrrolidone, alkyl, polyoxyalkylene, fluoroalkyl or amino moieties.

30. A skincare cosmetic material comprising the cosmetic material according to claim 1 as at least a part of constituents.

31. A hair-care cosmetic material comprising the cosmetic material according to claim 1 as at least a part of constituents.

32. An antiperspirant cosmetic material comprising the cosmetic material according to claim 1 as at least a part of constituents.

33. A makeup cosmetic material comprising the cosmetic material according to claim 1 as at least a part of constituents.

34. An UV protective cosmetic material comprising the cosmetic material according to claim 1 as at least a part of constituents.

35. A cosmetic material according to claim 1, which is prepared in a state selected from liquid, emulsion, cream, solid, paste, gel, powder, mousse or spray.

* * * * *